(12) United States Patent
Ban et al.

(10) Patent No.: US 11,554,047 B2
(45) Date of Patent: Jan. 17, 2023

(54) RADIATION DOSIMETRY SYSTEMS AND METHODS

(71) Applicant: LUTRONIC VISION INC., Burlington, MA (US)

(72) Inventors: Dayan Ban, Waterloo (CA); Mordehai Margalit, Zichron Yaakov (IL); Heechul Lee, Goyang-si (KR)

(73) Assignee: LUTRONIC VISION INC., Burlington, MA (US)

( * ) Notice: Subject to any disclaimer, the term of this patent is extended or adjusted under 35 U.S.C. 154(b) by 361 days.

(21) Appl. No.: 16/632,861

(22) PCT Filed: Jul. 21, 2017

(86) PCT No.: PCT/US2017/043387
§ 371 (c)(1),
(2) Date: Jan. 21, 2020

(87) PCT Pub. No.: WO2019/017975
PCT Pub. Date: Jan. 24, 2019

(65) Prior Publication Data
US 2020/0163798 A1    May 28, 2020

(51) Int. Cl.
*A61F 9/008* (2006.01)
(52) U.S. Cl.
CPC .......... *A61F 9/00808* (2013.01); *A61F 2009/00844* (2013.01); *A61F 2009/00863* (2013.01)
(58) Field of Classification Search
CPC .. A61F 9/008; A61F 9/00802; A61F 9/00821; A61F 9/00825; A61F 2009/00844; A61F 2009/00848; A61F 2009/00863
(Continued)

(56) References Cited
U.S. PATENT DOCUMENTS

| | | |
|---|---|---|
| 4,542,964 A | 9/1985 | Gilson et al. |
| 4,644,948 A | 2/1987 | Lang et al. |

(Continued)

FOREIGN PATENT DOCUMENTS

| | | |
|---|---|---|
| CN | 103592709 A | 2/2014 |
| CN | 104812340 A | 7/2015 |

(Continued)

OTHER PUBLICATIONS

"Light and Vision," Hyperphysics, accessed at https://web.archive.org/web/20161202153403/http://hyperphysics.phy-astr.gsu.edu/hbase/vision/eyescal.html, archived on Dec. 2, 2016, accessed on Jun. 14, 2017, pp. 4.

(Continued)

*Primary Examiner* — Ahmed M Farah

(57) ABSTRACT

In some examples, a laser-based ophthalmological surgical system (hereinafter "system") includes a therapeutic radiation source configured to emit therapeutic radiation with a first wavelength. The system may also include a probe radiation source configured to emit probe radiation with a second wavelength different than the first wavelength. The system may also include one or more optical elements configured to direct the therapeutic radiation and the probe radiation into an eye of a patient and to collect reflected probe radiation from the eye of the patient. The reflected probe radiation may be indicative of an amount of therapeutic radiation exposure of the eye of the patient. The system may also include a photodetector configured to receive the reflected probe radiation from the one or more optical elements and to generate a photocurrent indicative of the amount of therapeutic radiation exposure of the eye of the patient.

19 Claims, 11 Drawing Sheets

(58) Field of Classification Search
USPC .......................... 606/4–6, 10–12; 128/898
See application file for complete search history.

(56) References Cited

U.S. PATENT DOCUMENTS

| | | | |
|---|---|---|---|
| 4,848,894 A | 7/1989 | Buser et al. | |
| 5,954,711 A | 9/1999 | Ozaki et al. | |
| 6,634,753 B1 | 10/2003 | Rozenman | |
| 7,479,138 B2 * | 1/2009 | Hindi | H01S 3/1305 606/5 |
| 7,524,060 B2 | 4/2009 | Sanchez Ramos | |
| 7,947,036 B2 | 5/2011 | Lin | |
| 9,861,275 B2 | 1/2018 | Wellhoefer | |
| 2004/0039378 A1 * | 2/2004 | Lin | A61F 9/008 606/6 |
| 2010/0021983 A1 | 1/2010 | Vogel | |
| 2011/0184393 A1 * | 7/2011 | Brinkmann | A61F 9/008 606/4 |
| 2012/0302862 A1 | 11/2012 | Yun et al. | |
| 2018/0207029 A1 * | 7/2018 | Herekar | A61F 9/00825 |
| 2020/0261268 A1 * | 8/2020 | Margalit | A61B 18/18 |

FOREIGN PATENT DOCUMENTS

| | | |
|---|---|---|
| WO | 03/036834 A1 | 5/2003 |
| WO | 2010/031395 A1 | 3/2010 |

OTHER PUBLICATIONS

International Search Report and Written Opinion for International Application No. PCT/CN2017/112311 dated Aug. 10, 2018, pp. 08.
International Search Report and Written Opinion for International Application No. PCT/US2017/43387 dated Oct. 20, 2017, pp. 10.
Misaridis, T., and Jense, J.A., "Use of Modulated Excitation Signals in Medical Ultrasound. Part I: Basic Concepts and Expected Benefits," IEEE Transactions on Ultrasonics, Ferroelectrics, and Frequency Control, vol. 52, Issue 2, pp. 177-191 (Feb. 2005).
Roegener, J., et al., "Pump-probe detection of laser-induced microbubble formation in retinal pigment epithelium cells," Journal of Biomedical Optics, vol. 9, Issue 2, pp. 367-371 (Mar./Apr. 2004).
Varikooty, J., et al., "Measurement of the Refractive Index of Soft Contact Lenses During Wear," Eye & Contact Lens, vol. 36, No. 1, pp. 2-5 (Jan. 2010).
Schlott, Kerstin et al., "Automatic temperature controlled retinal photocoagulation," Journal of Biomedical Optics, vol. 17, No. 6, pp. 061223-1-061223-8 (Jun. 2012).

* cited by examiner

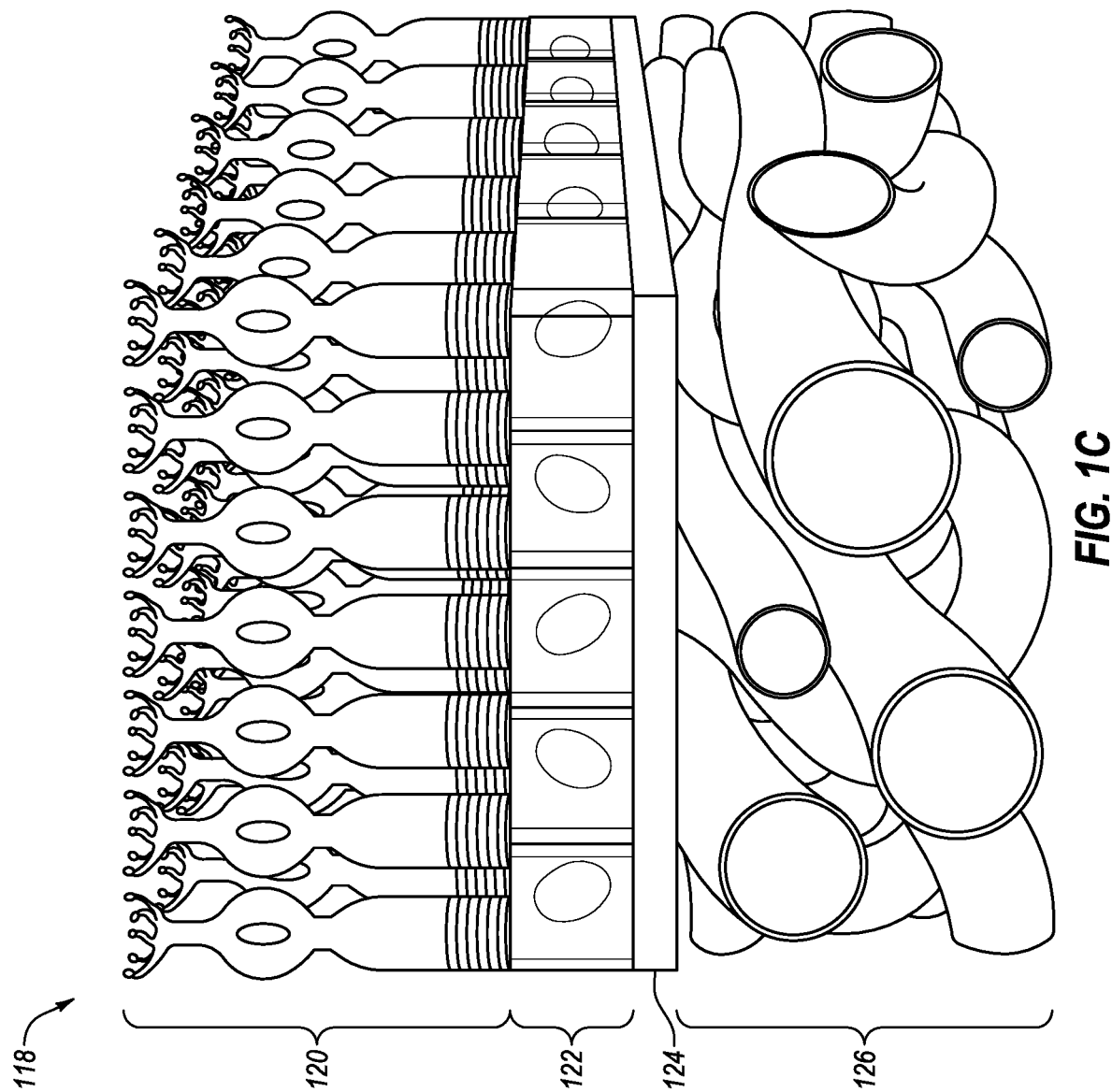

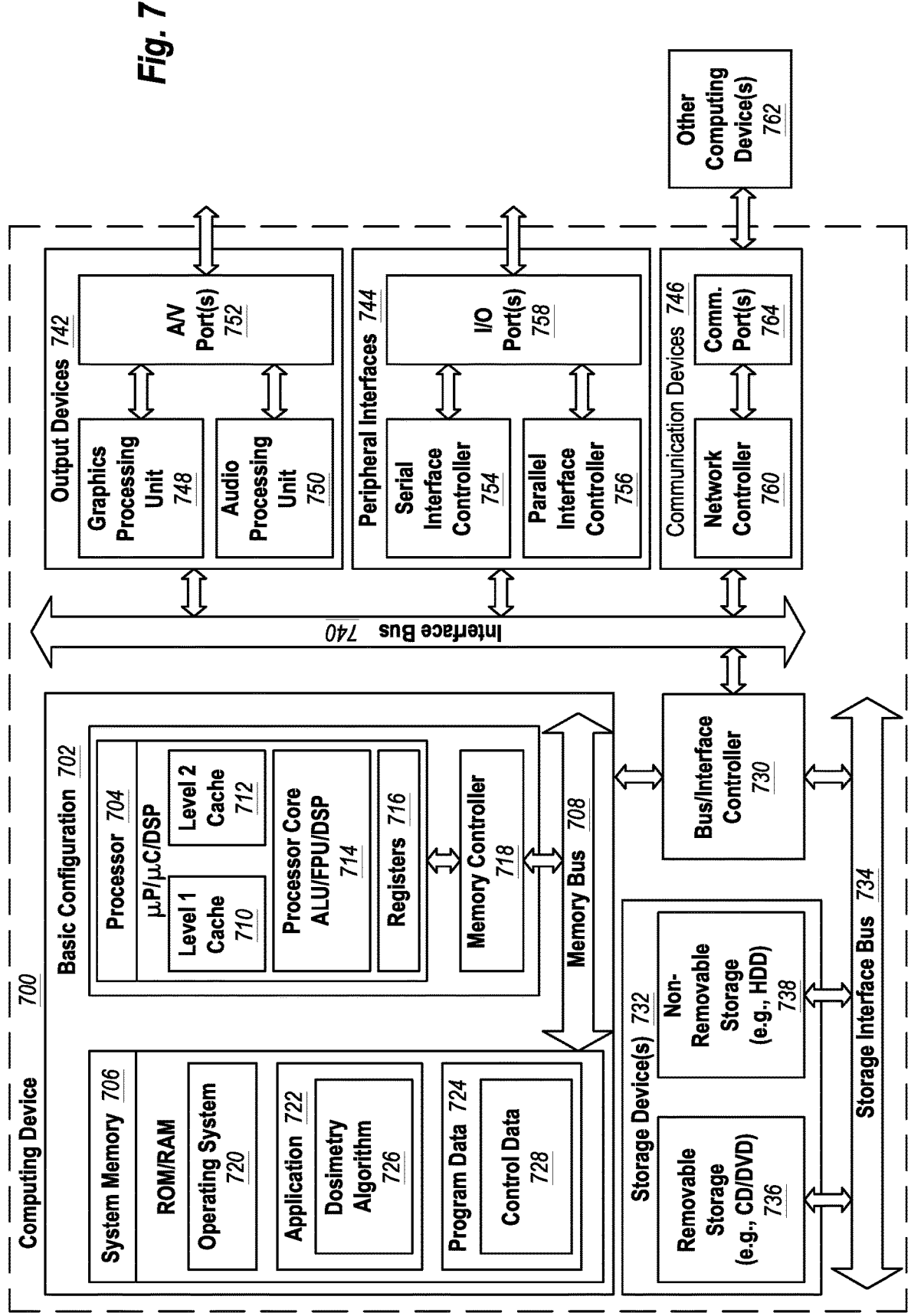

RADIATION DOSIMETRY SYSTEMS AND METHODS

CROSS-REFERENCE TO RELATED APPLICATIONS

This application is a § 371 National Stage of International Application No. PCT/2017/043387 filed on Jul. 21, 2017, which is incorporated herein by reference.

BACKGROUND

Unless otherwise indicated herein, the materials described herein are not prior art to the claims in the present application and are not admitted to be prior art by inclusion in this section.

Therapeutic radiation may be administered to an eye of a patient to treat various conditions of the eye that may negatively affect vision. It may be difficult to accurately measure an exposure level of the eye to the therapeutic radiation, which can damage the eye at excess exposure levels.

SUMMARY

Techniques described herein generally relate to radiation dosimeter systems and methods.

In an example embodiment, a laser-based ophthalmological surgical system (hereinafter "system") may include a therapeutic radiation source configured to emit therapeutic radiation with a first wavelength. The system may also include a probe radiation source configured to emit probe radiation with a second wavelength different than the first wavelength. The system may also include one or more optical elements configured to direct the therapeutic radiation and the probe radiation into an eye of a patient and to collect reflected probe radiation from the eye of the patient. The reflected probe radiation may be indicative of an amount of therapeutic radiation exposure of the eye of the patient. The system may also include a photodetector configured to receive the reflected probe radiation from the one or more optical elements and to generate a photocurrent indicative of the amount of therapeutic radiation exposure of the eye of the patient.

In another example embodiment, a method to measure therapeutic radiation dosimetry may include irradiating an eye of a patient with therapeutic radiation with a first wavelength. The therapeutic radiation may cause microbubbles to form on melanosomes of retinal pigment epithelial (RPE) cells of the eye of the patient. The method may also include irradiating the eye of the patient with probe radiation with a second wavelength different than the first wavelength. The method may also include collecting reflected probe radiation from the eye of the patient. The method may also include generating a photocurrent from the collected reflected probe radiation, the photocurrent being indicative of an amount of therapeutic radiation exposure of the eye of the patient.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE FIGURES

The foregoing and following information, as well as other features of this disclosure, will become more fully apparent from the following description and appended claims, taken in conjunction with the accompanying drawings. Understanding that these drawings depict only several embodiments in accordance with the disclosure and are, therefore, not to be considered limiting of its scope, the disclosure will be described with additional specificity and detail through use of the accompanying drawings:

FIG. 1C is a cross-sectional perspective view of a portion of the macula of FIG. 1B;

FIG. 7 illustrates a block diagram of an example computing device, all arranged in accordance with at least one embodiment of the present disclosure.

DETAILED DESCRIPTION

Figure 1A:
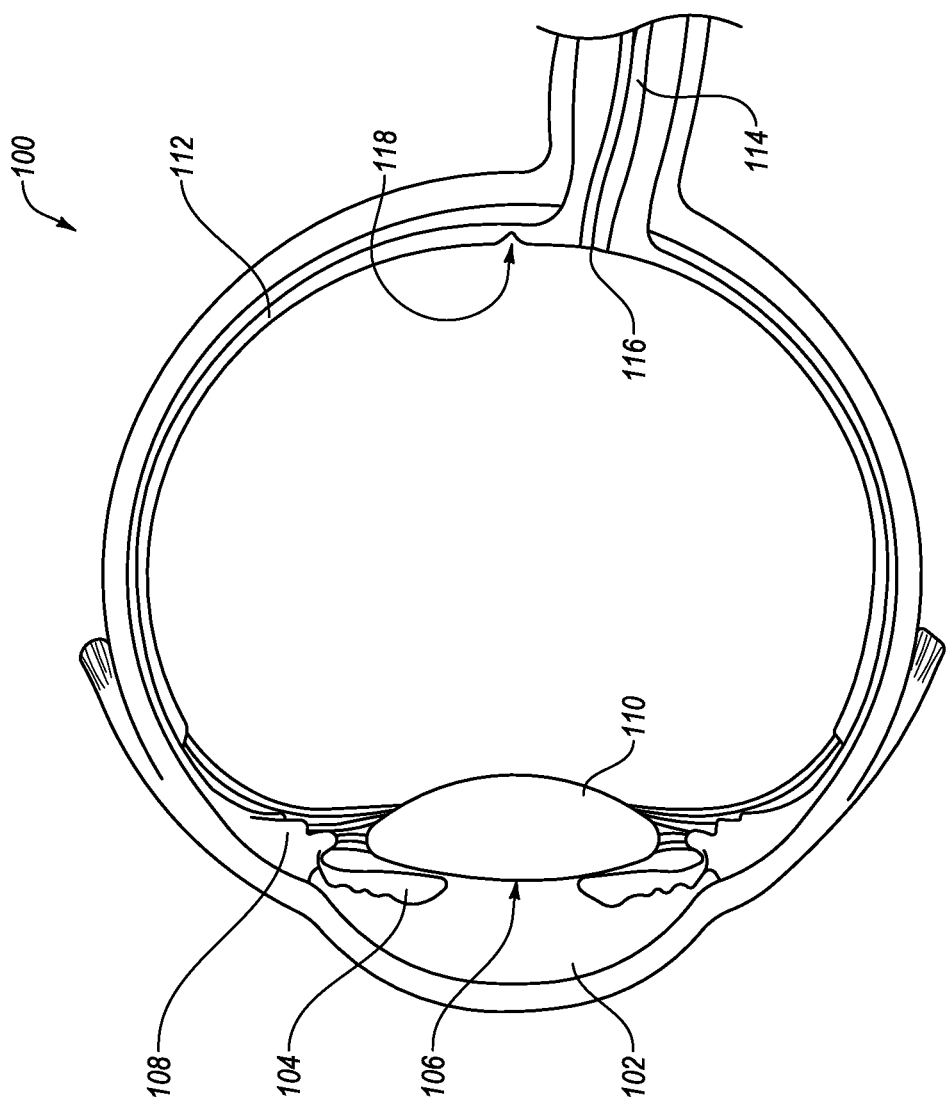
FIG. 1A is a cross-sectional view of an example human eye (hereinafter "eye")

This disclosure is generally drawn to methods, apparatus, systems, devices, and computer program products related to therapeutic radiation dosimetry.

A laser-based ophthalmological surgical system (hereinafter "system") in accordance with the present disclosure may include a therapeutic radiation source and a probe radiation source. The therapeutic radiation source may emit therapeutic radiation, which may be directed to a target area of an eye of a patient. The therapeutic radiation may induce a change in the target area of the eye of the patient, such as formation and/or bursting of microbubbles, which may be measured optically. The probe radiation source may emit probe radiation which may be directed to the target area of the eye of the patient, and which may be reflected by the target area of the eye of the patient. The probe radiation may have a different wavelength than the therapeutic radiation. The system may also include one or more optical elements configured to direct the therapeutic radiation and the probe radiation into the eye of the patient and to collect reflected probe radiation from the eye of the patient. The one or more optical elements may include one or more beam splitters and/or an optical filter. The optical filter may filter out radiation at the wavelength of the therapeutic radiation to reduce optical noise from reflected therapeutic radiation.

An intensity or other property of the reflected probe radiation may vary in accordance with the change induced in the target area of the patient, which change may depend on an exposure level of the eye of the patient to the therapeutic radiation. Thus, the reflected probe radiation may be measured as a proxy for the exposure level of the eye of the patient to the therapeutic radiation. In response to the reflected probe radiation reaching a threshold level corresponding to a threshold therapeutic radiation exposure level, administration of the therapeutic radiation to the eye of the patient may be terminated.

The system may implement a gating technique to improve signal to noise ratio in the measured reflected probe radiation to, e.g., limit data collection to time intervals of expected microbubble formation and/or bursting. Alternatively or additionally, a lock-in technique may be implemented with a narrow band pass filter in the system to filter out optical noise at frequencies other than a modulation frequency, e.g., pulse repetition rate, of the probe radiation.

In this detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented herein. The aspects of the present disclosure, as generally described herein, and illustrated in the Figures, can be arranged, substituted, combined, separated, and designed in a wide variety of different configurations, all of which are explicitly contemplated herein.

FIG. 1A is a cross-sectional view of an example human eye (hereinafter "eye") 100, arranged in accordance with at least one embodiment described herein. The eye 100 may include a cornea 102, an iris 104, a pupil 106, a ciliary body 108, a lens 110, a retina 112, and an optic nerve 114. The retina 112 generally includes a light-sensitive layer of tissue upon which optics of the eye 100 project an image of the visual world external to the eye 100. Through a series of chemical and electrical events nerve impulses may be triggered in response to light striking the retina 112. The nerve impulses may be processed in vision centers of the brain such that the visual world may be perceived by a person.

As illustrated in FIG. 1A, the retina 112 includes an optic disc 116, sometimes referred to as the "blind spot", and a macula 118 temporal to the optic disc 116.

Figure 1B:
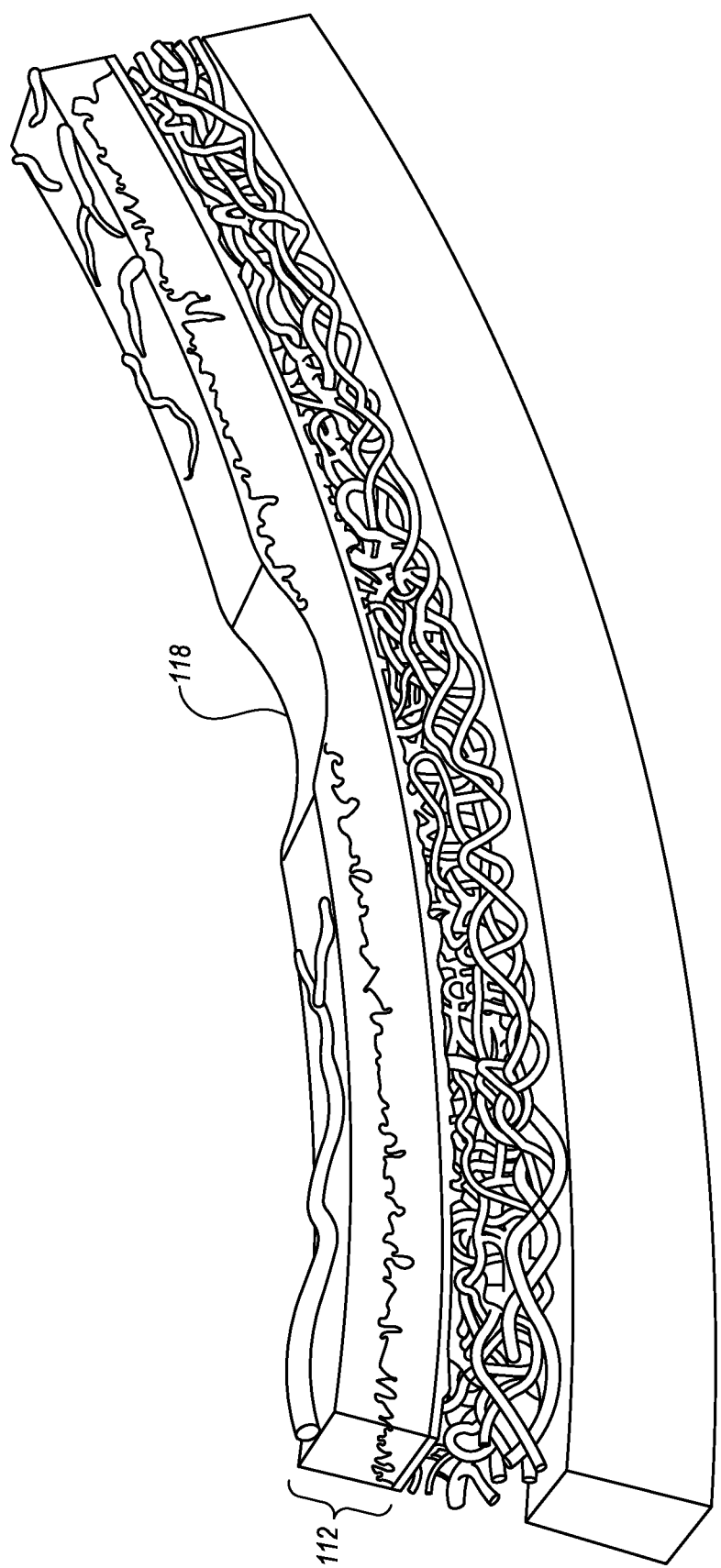
FIG. 1B is a cross-sectional perspective view of a portion of a retina and macula of FIG. 1B.

FIG. 1B is a cross-sectional perspective view of a portion of the retina 112 and the macula 118 of FIG. 1A, arranged in accordance with at least one embodiment described herein.

FIG. 1C is a cross-sectional perspective view of a portion of the macula 118 of FIG. 1B, arranged in accordance with at least one embodiment described herein. FIG. 1C depicts various layers that may make up the macula 118, including photoreceptors 120, retinal pigment epithelial (RPE) cells 122, Bruch's membrane 124, and choroid 126. The macula 118 may have a relatively high concentration of photoreceptors 120 compared to the rest of the retina 112 and without blood vessels, for central and/or high resolution vision. The RPE cells 122 may nourish the photoreceptors 120 by supplying nutrients from the choroid 126 and transporting extracellular material out through the Bruch's membrane 124.

Various conditions may adversely affect vision in the eye 100. For instance, with reference to FIGS. 1A-1C, age-related macular degeneration (AMD) may involve degradation of the RPE cells 122 in the macula 118. In dry AMD, degraded RPE cells 122 may fail to transport extracellular material which may then begin to build up ("Drusen") in between the Bruch's membrane 124 and the RPE cells 122. The Drusen may interfere with the supply of nutrients to the photoreceptors 120, which can lead to vision loss. In wet AMD, new blood vessels (neovascularization) may grow from the choroid 126 and penetrate the Bruch's membrane 124 and the RPE cells 122 to supply nutrients to the photoreceptors 120. The new blood vessels may be weak and prone to bleeding and leakage, which may result in blood and protein leakages, which in turn may damage the photoreceptors 120 and fuel rapid vision loss.

Another condition that may adversely affect vision in the eye 100 may be diabetic macular edema (DME). In more detail, persons with diabetes may experience a slowing of metabolism over time, which may reduce the ability of retinal vessels to deliver enough nutrients, which in turn may induce neovascularization. Fluid leakage from the neovascularization may cause the retina 112 to swell, causing vision loss.

Another condition that may adversely affect vision in the eye 100 may be central serous chorioretinopathy (CSC). In CSC, leakage of fluid accumulates under the central macula 118, resulting in blurred or distorted vision which may progressively decline with each recurrence.

Some embodiments described herein include a laser-based ophthalmological surgical system that includes a therapeutic radiation source configured to emit therapeutic radiation to treat AMD, DME, CSC, and/or other conditions of the eye 100. In general, the therapeutic radiation may be absorbed by RPE cells 122 targeted with the therapeutic radiation. Specifically, the therapeutic radiation may be absorbed by melanin or other chromophore in the RPE cells 122. The absorbed therapeutic radiation may be converted to heat, which may lead to formation of microbubbles in the RPE cells 122. The microbubbles may burst or otherwise destroy RPE cells 122. By targeting degraded RPE cells included in the RPE cells 122, the degraded RPE cells can be destroyed to prevent them from causing further damage.

According to some embodiments, such laser-based ophthalmological surgical systems may use real-time feedback to detect RPE damage and stop therapeutic radiation automatically based on the feedback prior to excessively damaging the targeted RPE cells 122. In an example embodiment, the therapeutic radiation is administered to the targeted RPE cells 122 in pulses with a pulse duration in a range from 1.6 microseconds to 1.8 microseconds. The administration of the therapeutic radiation may be periodic in some embodiments, with a pulse frequency in a range from 50 hertz (Hz) to 200 Hz (corresponding to a period in a range of 0.02 seconds to 0.005 seconds), such as about 100 Hz (corresponding to a period of 0.01 seconds). For instance, multiple therapeutic radiation pulses, each with a pulse duration of 1.7 microseconds, may be sequentially administered with a pulse frequency of 100 Hz. The administration of pulses may be terminated in response to the feedback indicating a maximum exposure to the therapeutic radiation. In other embodiments, the pulse frequency of the therapeutic radiation may be greater than 200 Hz.

The therapeutic radiation may in some embodiments be generally more effective at treating conditions of the eye at higher exposure levels, However, at a particular level of exposure (e.g., power) to the therapeutic radiation, therapeutic radiation may cause excessive damage to the eye that may result in vision loss. To avoid or reduce the likelihood of vision loss due to excessive exposure to the therapeutic radiation while permitting exposure up to a sufficiently high level to be effective, some embodiments described herein may start administration of the therapeutic radiation at a relatively low exposure that ramps up with each successive pulse until real-time feedback indicates a threshold exposure has been reached. In an example, the first pulse of therapeutic radiation may be at about 50% of a relatively high energy level, such as a maximum energy level. More generally, the first pulse may be at a relatively low energy level, and each successively administered pulse of therapeutic radiation may be increased compared to the preceding pulse. The amount of increase from pulse to pulse may be fixed or variable. For instance, in an example embodiment, the amount of increase from pulse to pulse may be fixed at 5% of the relatively high energy level.

The real-time feedback may measure exposure of the targeted RPE cells to the therapeutic radiation by measuring the formation and/or bursting of microbubbles that form on melanosomes of the targeted RPE cells in response to exposure to the therapeutic radiation. In an example embodiment, the formation and/or bursting of the microbubbles may be measured with optical feedback and/or acoustic feedback. In particular, the targeted RPE cells may reflect and/or emit optical and/or acoustic signals that may vary depending on the presence, absence, and/or characteristics (e.g., size, velocity) of the microbubbles. Excessive exposure to the therapeutic radiation after microbubble formation and RPE damage could damage other retinal structures, which may lead to formation of scotoma on the retina.

Figure 2:
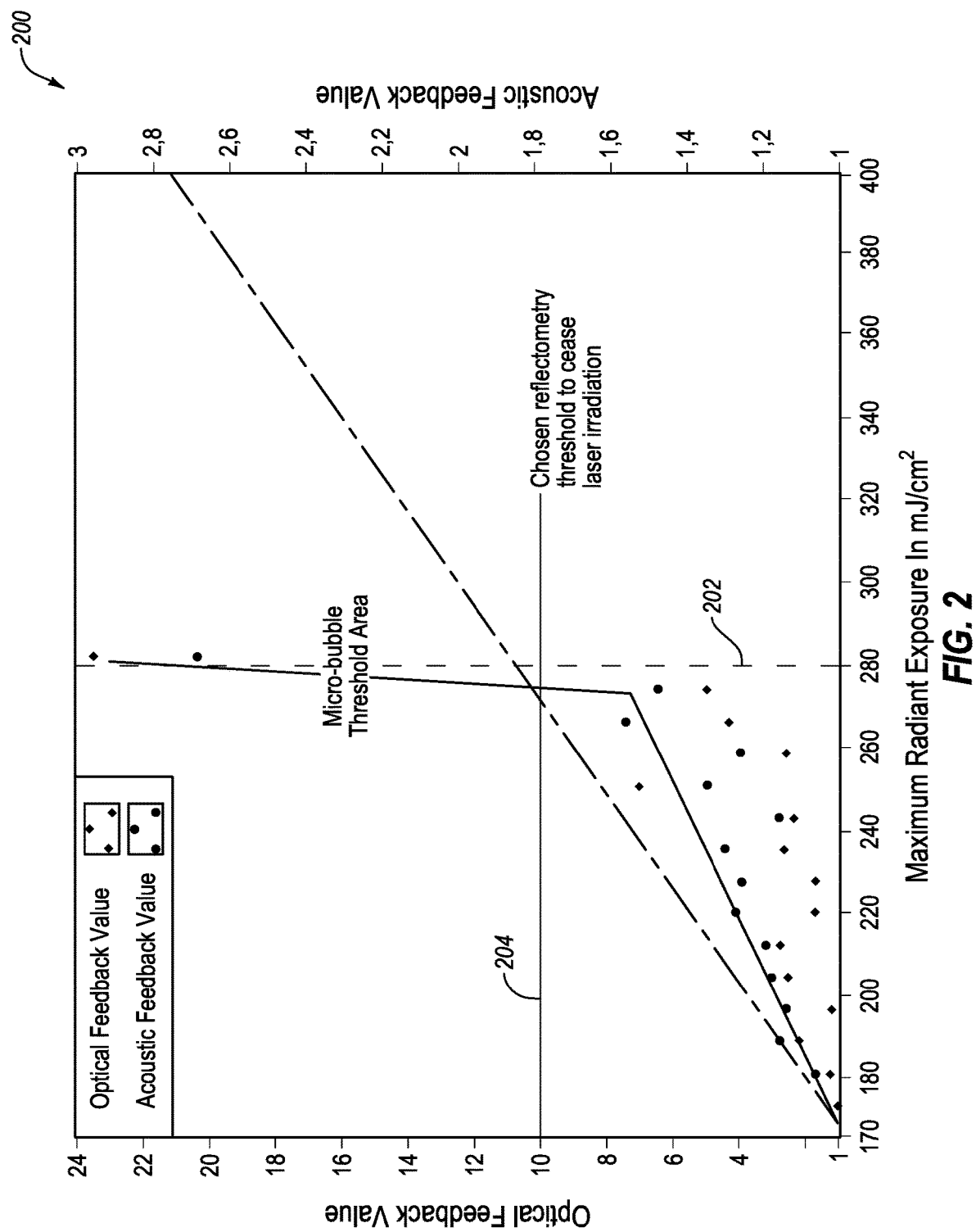
FIG. 2 is a graphical representation of an example feedback response to therapeutic radiation that may be generated by a laser-based ophthalmological surgical system.

FIG. 2 is a graphical representation 200 of an example feedback response to therapeutic radiation that may be generated by a laser-based ophthalmological surgical system, arranged in accordance with at least one embodiment described herein. The horizontal axis is radiant exposure to the therapeutic radiation in millijoules per square centimeter ($mJ/cm^2$), the left vertical axis is optical feedback value in microwatts, and the right axis is acoustic feedback value in volts. FIG. 2 includes data points representing the measured optical feedback (diamonds in FIG. 2) and acoustic feedback (circles in FIG. 2) as a function of therapeutic radiation exposure level. Each data point may represent a measurement of the optical or acoustic feedback from the targeted RPE cells and/or from microbubbles thereon after exposure to a pulse of the therapeutic radiation at a corresponding exposure level. All of the optical feedback data points may be collectively referred to as an optical signal and all of the acoustic feedback data points may be collectively referred to as an acoustic signal.

FIG. 2 additionally includes a vertical reference zone 202, at around 280 $mJ/cm^2$ in the example of FIG. 2, that represents a microbubble threshold area at a therapeutic radiation exposure level that may be known or expected to cause excessive damage to the targeted RPE cells. FIG. 2 additionally includes a horizontal reference line 204 at a threshold optical feedback value, at 10 arbitrary units (a.u.) in the example of FIG. 2, which may be selected as an optical feedback value after which irradiation with the therapeutic radiation may be terminated to avoid or reduce the likelihood of excessive damage to the targeted RPE cells.

The optical signal in the example of FIG. 2 may be generated by measuring reflected therapeutic radiation from the targeted RPE cells and/or from microbubbles that form thereon. As illustrated in FIG. 2, the optical signal in this example is somewhat noisy and exhibits substantial fluctuations, particularly around the vertical reference zone 202. This strong fluctuation in the measured optical signal may impose a difficulty in accurately determining when the optical signal is at or near the threshold optical feedback value.

Embodiments described herein may improve the noise level of the reflected optical signal. Rather than directly using the reflected signal from the therapeutic radiation, a separate probe radiation may be introduced into a laser-based ophthalmological surgical system. The probe radiation may be at a different wavelength than the therapeutic radiation. The probe radiation may be modulated at a modulation frequency. The probe radiation may be reflected by the RPE cells with or without the formation of microbubbles. A difference in the reflected signal from the probe radiation (the differential reflectometry signal) may be measured and may be used as a more accurate indicator for the formation of the micro-bubbles than the reflected signal from the therapeutic radiation. A gating technique may be deployed to collect the differential reflectometry signal. A lock-in amplifier technique may be optionally employed to further improve a signal-to-noise ratio in the reflectance measurement. Thus, the observed optical signal fluctuation illustrated in and described with respect to FIG. 2 may be suppressed.

Figure 3A:
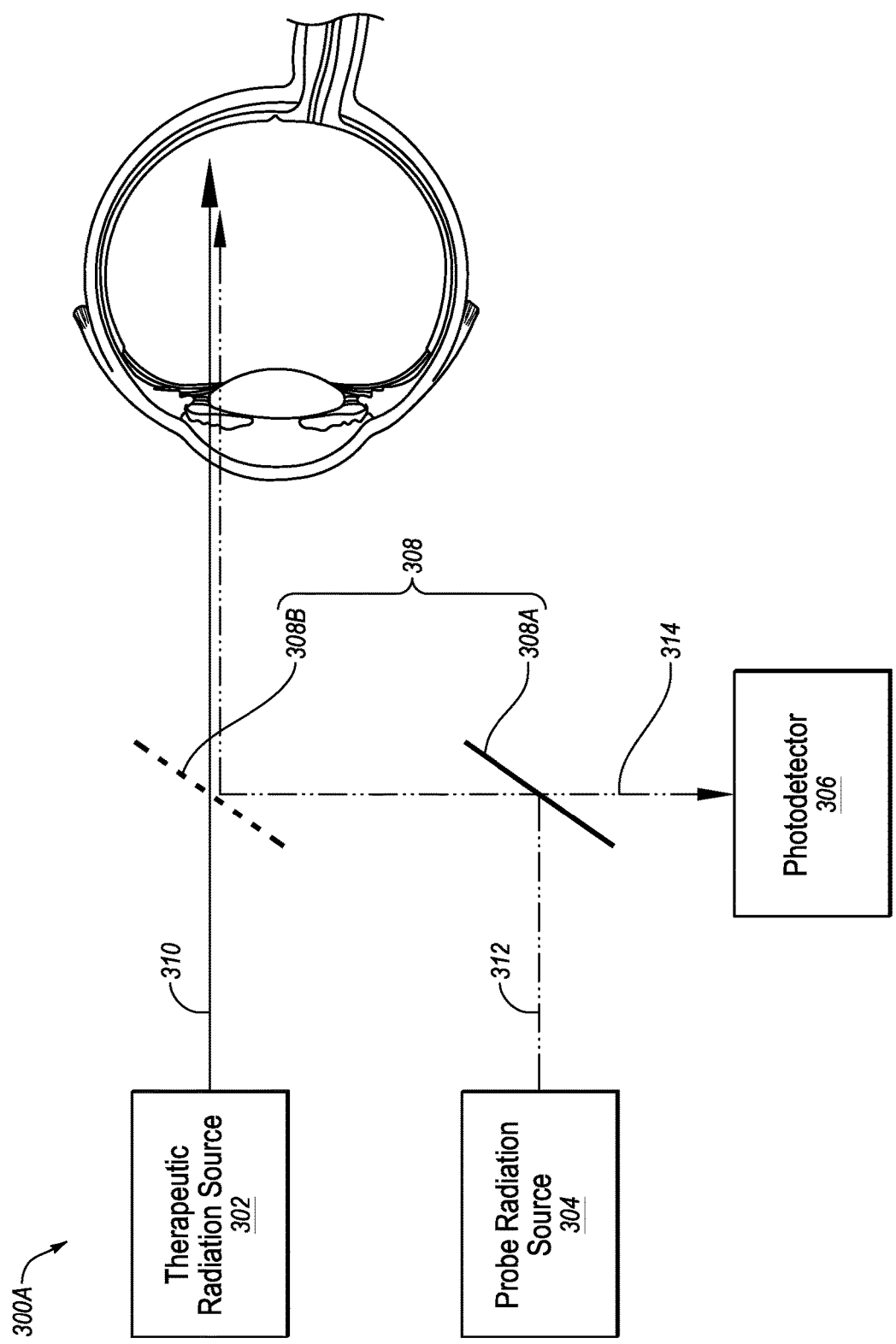
FIG. 3A is a block diagram of an example laser-based ophthalmological surgical system (hereinafter "system")

In more detail, FIG. 3A is a block diagram of an example laser-based ophthalmological surgical system (hereinafter "system") 300A, arranged in accordance with at least one embodiment described herein. The system 300A may include a therapeutic radiation source 302, a probe radiation source 304, a photodetector 306, and one or more optical elements 308. The system may include one or more other elements not depicted in FIG. 3A for simplicity, such as one or more acoustic detectors, an imaging system (e.g., microscope), bias and/or modulation circuitry, and/or other elements.

The therapeutic radiation source 302 may be configured to emit therapeutic radiation 310 with a first wavelength. For instance, the therapeutic radiation 310 with the first wavelength may include therapeutic radiation with a center wavelength in a range from 430-500 nanometers (nm), or in a range from 520 nm to about 540 nm, such as 527 nm, or in a range from 575 nm or higher, such as 577 nm, or in some other range. The therapeutic radiation 310 in some embodiments may be pulsed, meaning the therapeutic radiation source 302 may emit the therapeutic radiation 310 as discrete pulses. The pulses of therapeutic radiation 310 may each have a pulse duration in a range from 1.6 microseconds to 1.8 microseconds, and may be administered periodically in some embodiments, with a pulse frequency in a range of 50 Hz to 200 Hz or higher (e.g., 500 Hz), such as 100 Hz. As used herein, "pulse frequency" may refer to a frequency at which the discrete pulses of therapeutic radiation 310 are emitted by the therapeutic radiation source 302, e.g., a repetition rate of the discrete pulses of therapeutic radiation 310. The pulses of therapeutic radiation 310 may be substantially flat-topped or may have some other shape.

In some embodiments, the therapeutic radiation 310 emitted by the therapeutic radiation source 302 may have up to a maximum energy of at least 0.4 millijoules (mJ). The therapeutic radiation source 302 may be controlled to emit discrete pulses of the therapeutic radiation 310 that have an energy per pulse (hereinafter "pulse energy") in a range between 0 mJ up to the maximum energy. For instance, the discrete pulses of therapeutic radiation 310 may be sequentially ramped up beginning at a relatively low pulse energy (e.g., 50% of the maximum energy) and successively ramping up in pulse energy by a fixed or variable amount (e.g., 5% of the maximum energy) until optical and/or acoustic feedback indicates a threshold exposure level of the eye 100 to the therapeutic radiation 310 has been reached.

The probe radiation source 304 may be configured to emit probe radiation 312 with a second wavelength that is different than the first wavelength of the therapeutic radiation 310. In some embodiments, the probe radiation source 304 may include a targeting optical source already included in some legacy laser-based ophthalmological surgical systems and/or other laser-based ophthalmological surgical systems to optically align the therapeutic radiation source 302 to a target area of RPE cells in the eye 100 prior to irradiation with the therapeutic radiation 310. Such laser-based ophthalmological surgical systems may be modified to use the targeting optical source as the probe radiation source 304 as described herein. In these and other embodiments, the probe radiation 312 with the second wavelength may generally include radiation with a center wavelength that is different than the first wavelength of the therapeutic radiation and that can be detected by the photodetector 306, such as radiation with a center wavelength in a range from 590 nm to 1 micrometer. For instance, the probe radiation 312 may include radiation with a center wavelength in a red portion, e.g., 620 nm to 750 nm, of the visible spectrum, and/or in an orange portion, e.g., 590 nm to 620 nm, of the visible spectrum. As a particular example, the probe radiation 312 with the second wavelength may include radiation with a center wavelength of 630 nm.

Alternatively or additionally, the probe radiation source 304 may be included in the system 300A instead of or in addition to a targeting optical source of the system 300A. In these and other embodiments, the probe radiation 312 with the second wavelength may include radiation with a center wavelength in one or more ranges of the infrared (IR) spectrum, such as 0.75 micrometers to 1.7 micrometers or even up to 2.5 micrometers and/or 6 micrometers to 10 micrometers. For instance, the probe radiation 312 with the second wavelength may include radiation with a center wavelength of 1.55 micrometers.

Similar to the therapeutic radiation 310, the probe radiation 312 may be pulsed, or emitted as discrete pulses. In some embodiments, the discrete pulses of probe radiation 312 may each have a pulse duration that is longer than the pulse duration of the discrete pulses of therapeutic radiation 310, as described with respect to FIG. 5B. For instance, the discrete pulses of probe radiation 312 may each have a pulse duration in a range from four microseconds to sixteen microseconds, such as eight microseconds. In these and other embodiments, the discrete pulses of probe radiation 312 may have a repetition rate equal to the repetition rate of the discrete pulses of therapeutic radiation 310 or equal to twice the repetition rate of the discrete pulses of therapeutic radiation 310. For instance, the discrete pulses of probe radiation 312 may have a repetition rate of 100 Hz or 200 Hz in some embodiments.

Figure 5A:
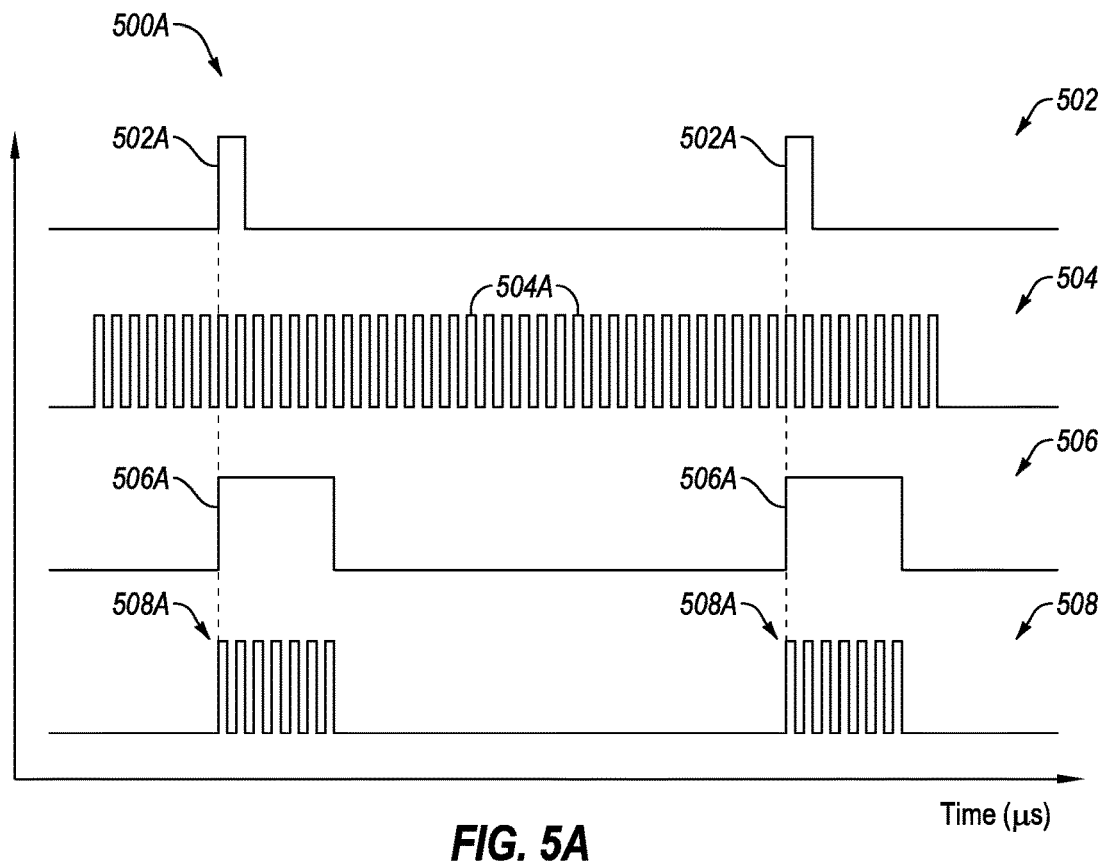
FIGS. 5A-5C illustrate first, second, and third example radiation timing sequences that may be implemented by one or both of the systems of FIGS. 3A and 3B.

In some embodiments, the discrete pulses of probe radiation 312 may each have a pulse duration that is shorter than the pulse duration of the discrete pulses of therapeutic radiation 310, as described with respect to FIG. 5A. For instance, the discrete pulses of probe radiation 312 may be emitted at a repetition rate in a range from 5 megahertz (MHz) to 20 MHz, such as 10 MHz, in which case each of the discrete pulses of probe radiation 312 may have a pulse duration in a range greater than zero and less than 0.1 microseconds. More generally, the discrete pulses of probe radiation 312 may be emitted at a repetition rate in a range from 100 kilohertz (kHz) to 100 MHz or even higher than 100 MHz.

Figure 5B:
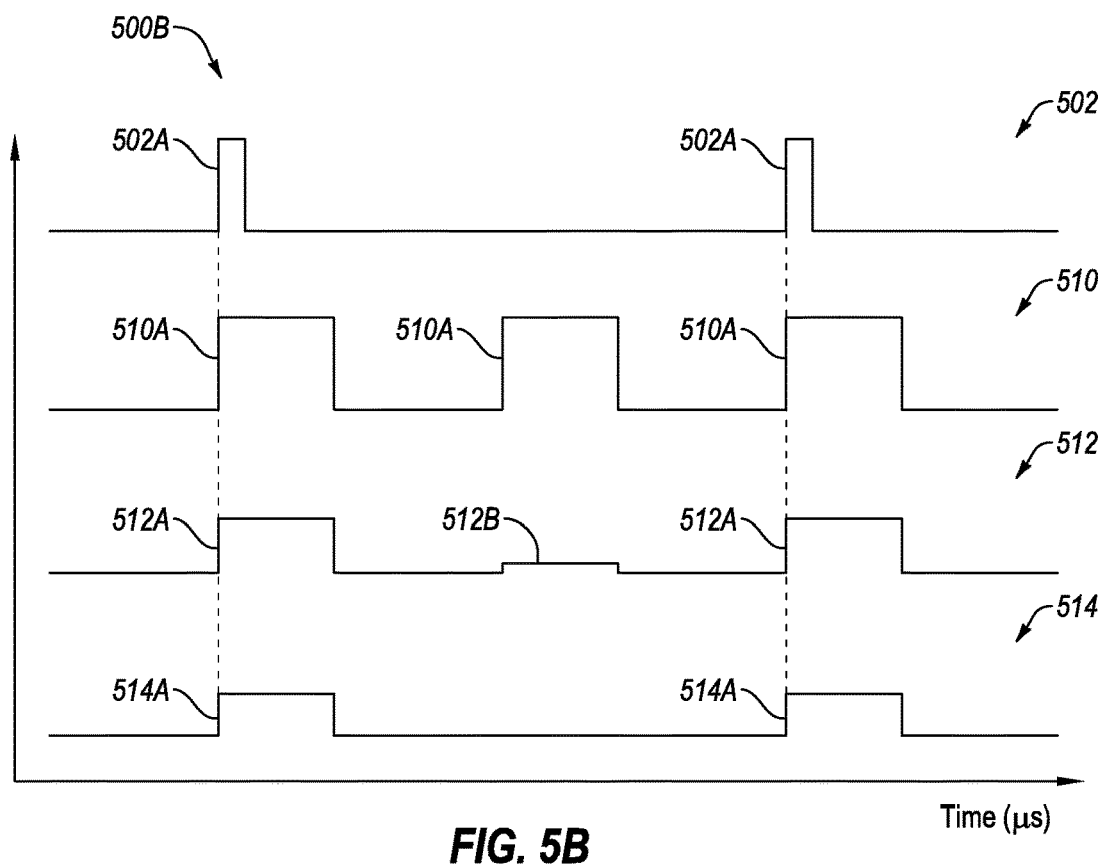
Figure 5C:
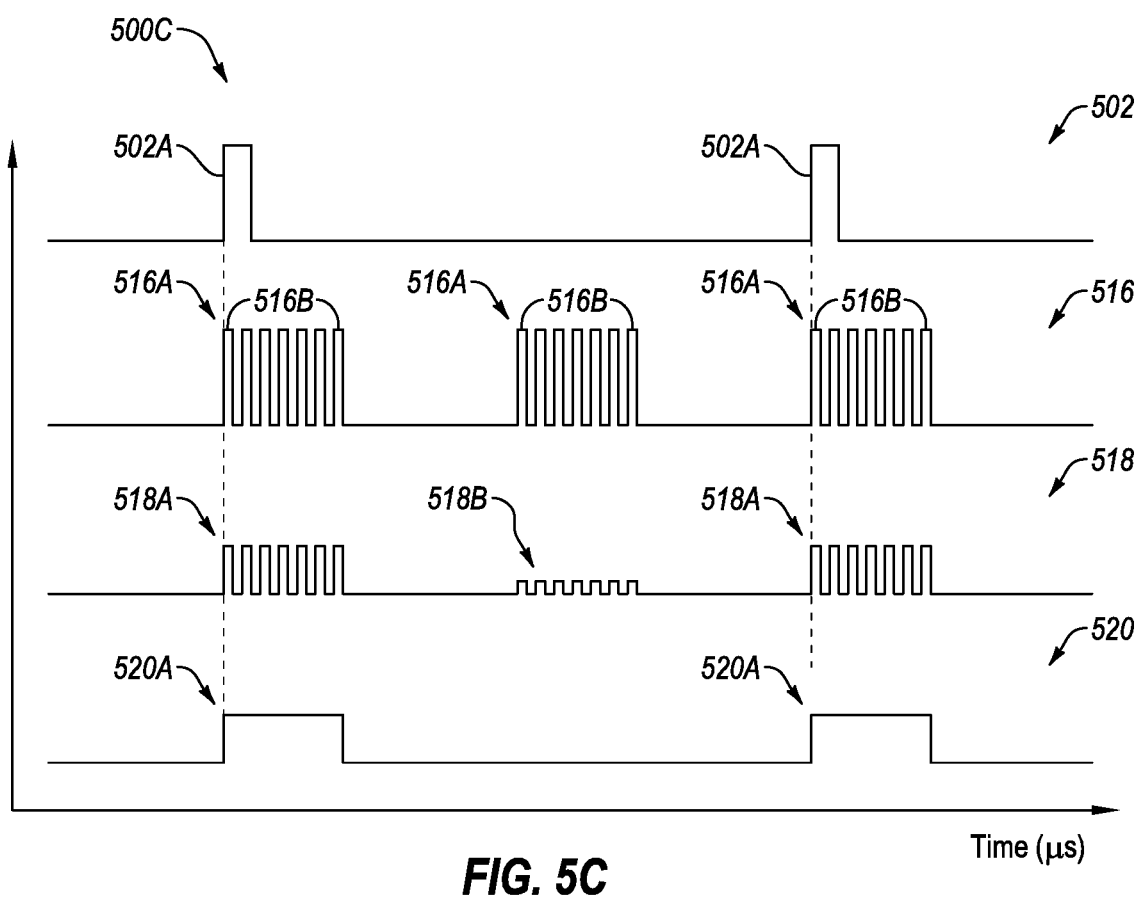

In other embodiments, the probe radiation source 304 is double modulated to emit the probe radiation 312 as pulse trains that have a pulse train repetition rate and a pulse train duration, where each pulse train includes discrete pulses at a pulse repetition rate, as described with respect to FIG. 5C. The pulse train repetition rate may be equal to the repetition rate of the discrete pulses of therapeutic radiation 310 or equal to twice the repetition rate of the discrete pulses of therapeutic radiation 310. For instance, the pulse trains of probe radiation 312 may have a repetition rate of 100 Hz or 200 Hz in some embodiments. The pulse train duration may be in a range from four microseconds to sixteen microseconds, such as eight microseconds. The discrete pulses that make up each pulse train may have a pulse repetition rate in a range from 5 megahertz (MHz) to 20 MHz, such as 10 MHz. More generally, the discrete pulses that make up each pulse train may have a pulse repetition rate in a range from 100 kHz to 100 MHz or even higher than 100 MHz.

The one or more optical elements 308 may be configured to direct the therapeutic radiation 310 and the probe radiation 312 into the eye 100 of a patient and to collect reflected probe radiation 314 from the eye 100 of the patient. As described elsewhere, the reflected probe radiation 314 may be indicative of an amount of therapeutic radiation exposure of the eye 100 of the patient. An area of the eye 100 to which the therapeutic radiation 310 is intended to be directed may be referred to as a target area. The one or more optical elements 308 may direct the therapeutic radiation 310 to the target area. The one or more optical elements 308 may also direct the probe radiation 312 to at least a portion of the target area. Thus, the probe radiation 312 may irradiate a first area within a second area irradiated by the therapeutic radiation 310 at overlapping and/or non-overlapping times.

The system 300A includes a first optical path of the probe radiation 312 between the probe radiation source 304 and the eye 100. The system 300A additionally includes a second optical path of the therapeutic radiation 310 between the therapeutic radiation source 302 and the eye 100. In some embodiments, the one or more optical elements 308 may include a first beam splitter 308A and a second beam splitter 308B.

The first beam splitter 308A is positioned in the first optical path of the probe radiation 312 between the probe radiation source 304 and the eye 100 of the patient. In the example of FIG. 3A, the first beam splitter 308A may be configured to reflect at least a portion of the probe radiation 312 from the probe radiation source 304 toward the eye 100 and to pass at least a portion of the reflected probe radiation 314 to the photodetector 306. In other embodiments, locations of the probe radiation source 304 and the photodetector 306 relative to the first beam splitter 308A may be swapped, as described with respect to FIG. 3B. In these and other embodiments, the first beam splitter 308A may include a 50/50 splitter at the second wavelength of the probe radiation 312.

The second beam splitter 308B is positioned in the second optical path of the therapeutic radiation 310 between the therapeutic radiation source 302 and the eye 100 of the patient and in the first optical path between the first beam splitter 308A and the eye 100 of the patient. In the example of FIG. 3A, the second beam splitter 308B may be configured to pass at least a portion of the therapeutic radiation 310 from the therapeutic radiation source 302, reflect at least a portion of the probe radiation 312 toward the eye 100 of the patient, and reflect at least a portion of the reflected probe radiation 314 collected from the eye 100 of the patient toward the first beam splitter 308A. In these and other embodiments, the second beam splitter 308B may include a dichroic splitter configured to pass the therapeutic radiation 310 at the first wavelength and reflect the probe radiation 312 and the reflected probe radiation 314, at the second wavelength.

The photodetector 306 may be configured to receive the reflected probe radiation 314 from the one or more optical elements 308 and to generate a photocurrent indicative of the amount of therapeutic radiation exposure of the eye 100 of the patient. In these and other embodiments, a magnitude of the photocurrent may depend on an intensity or other characteristic of the reflected probe radiation 314, which in turn may depend on the presence, absence, and/or characteristics (e.g., size, velocity) of microbubbles, which in turn may depend on the therapeutic radiation exposure of the eye 100 of the patient. In some embodiments, the photodetector 306 may include a silicon-based positive-intrinsic-negative (PIN) diode, an avalanche photodiode (APD), or other suitable optical receiver.

Figure 3B:
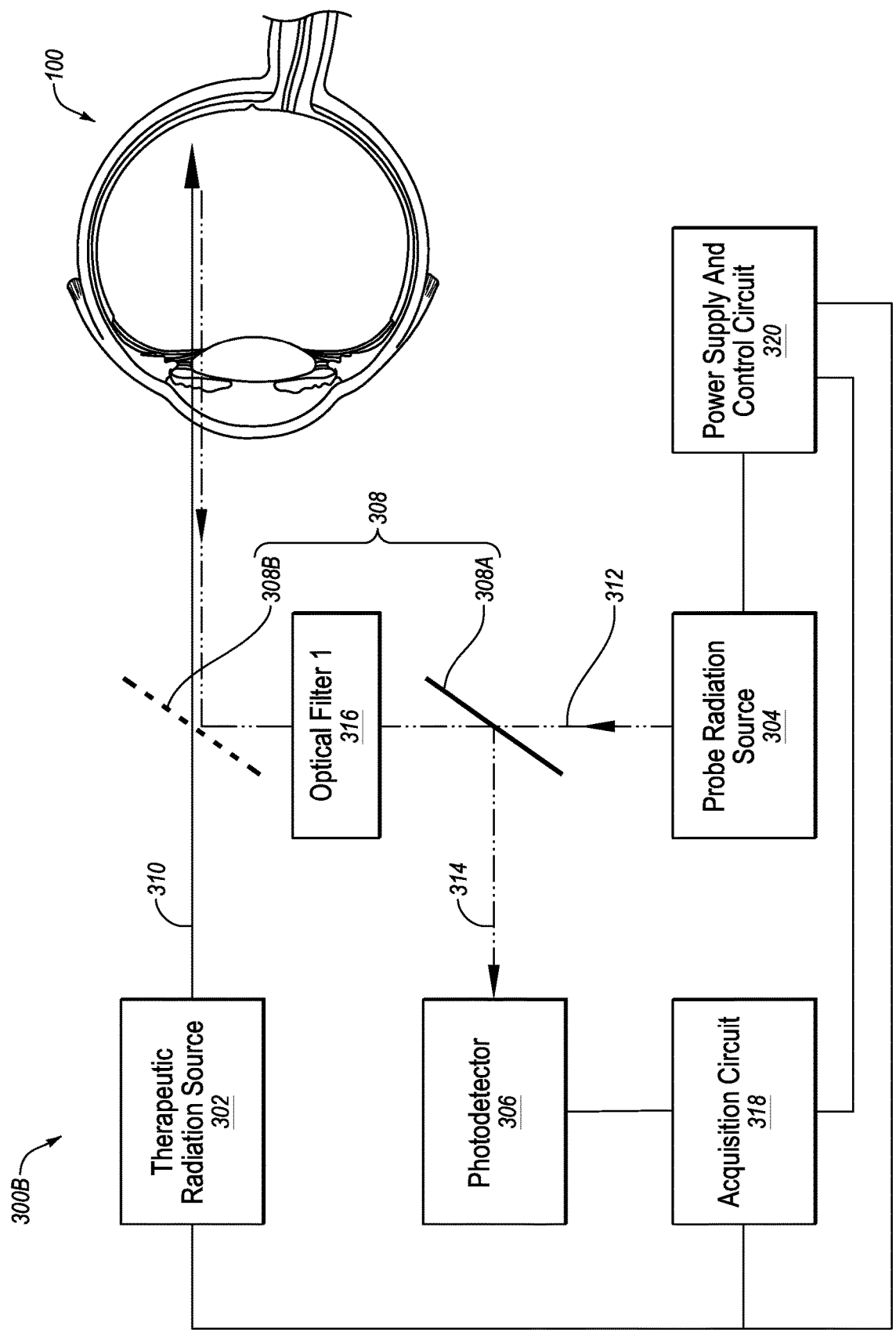
FIG. 3B is a block diagram of another example laser-based ophthalmological surgical system (hereinafter "system")

FIG. 3B is a block diagram of another example laser-based ophthalmological surgical system (hereinafter "system") 300B, arranged in accordance with at least one embodiment described herein. The system 300B may include the therapeutic radiation source 302, the probe radiation source 304, the photodetector 306, and the one or more optical elements 308, all of which are generally operated and/or configured in a same or similar manner as in FIG. 3A. The system 300B may include one or more other elements not depicted in FIG. 3B for simplicity, such as one or more acoustic detectors, an imaging system (e.g., microscope), bias and/or modulation circuitry, and/or other elements.

Compared to FIG. 3A, in FIG. 3B, locations of the probe radiation source 304 and the photodetector 306 have been swapped relative to the first beam splitter 308A. Accordingly, in FIG. 3B, the first beam splitter 308A may be configured to pass at least a portion of the probe radiation 312 from the probe radiation source 304 and to reflect at least a portion of the reflected probe radiation 314 toward the photodetector 306.

Compared to FIG. 3A, the system 300B of FIG. 3B may further include one or more of an optical filter 316, an acquisition circuit 318, and a power supply and control circuit 320.

As illustrated in FIG. 3A, the optical filter 316 may be positioned in the first optical path between the first beam splitter 308A and the second beam splitter 308B. The optical filter 316 may be configured to pass the probe radiation 312 and the reflected probe radiation 314 and to block the therapeutic radiation 310 from passing. For instance, the optical filter 316 may have a transmittance of at least 70%, 80%, 90%, 95%, or higher with respect to the probe radiation 312 and the reflected probe radiation 314 and may have a transmittance less than 10%, 5%, or lower with respect to the therapeutic radiation 310.

The acquisition circuit 318 may be electrically coupled to at least one of the therapeutic radiation source 302 (or a control circuit of the therapeutic radiation source), the photodetector 306, and the power supply and control circuit 320. The acquisition circuit 318 may be configured to process and/or convert photocurrent generated by the photodetector 306 to one or more optical feedback values, such as the optical feedback values graphically illustrated in FIG. 2. The acquisition circuit 318 may be configured to gate the photodetector 306 according to expected time intervals of microbubble formation and/or bursting. For instance, the acquisition circuit 318 may gate the photodetector 306 so that the photodetector 306 generates photocurrent only during expected time intervals of microbubble formation and/or bursting without generating photocurrent during other time intervals.

The therapeutic radiation source 302 may include or be coupled to a control circuit (not shown separately) of the therapeutic radiation source 302 to which the acquisition circuit 318 may also be electrically coupled. The control circuit of the therapeutic radiation source 302 may be configured to operate the therapeutic radiation source 302 to emit discrete pulses of the therapeutic radiation 310. The control circuit of the therapeutic radiation source 302 may generate and send a trigger signal to the acquisition circuit 318. The trigger signal may indicate when the discrete pulses of therapeutic radiation 310 are being emitted. The acquisition circuit 318 may be configured to receive the trigger signal from the control circuit of the therapeutic radiation source 302 to gate the photodetector 306 to generate photocurrent beginning when the therapeutic radiation source begins emitting a pulse of the therapeutic radiation and terminating after a first duration that is longer than a second duration of the pulse of the therapeutic radiation 310. The first duration during which the photodetector 306 is gated to generate photocurrent may be in a range from four microseconds to sixteen microseconds, such as eight microseconds, while the second duration of the pulse of the therapeutic radiation 310 may be in a range from 1.6 microseconds to 1.8 microseconds.

Figure 4:
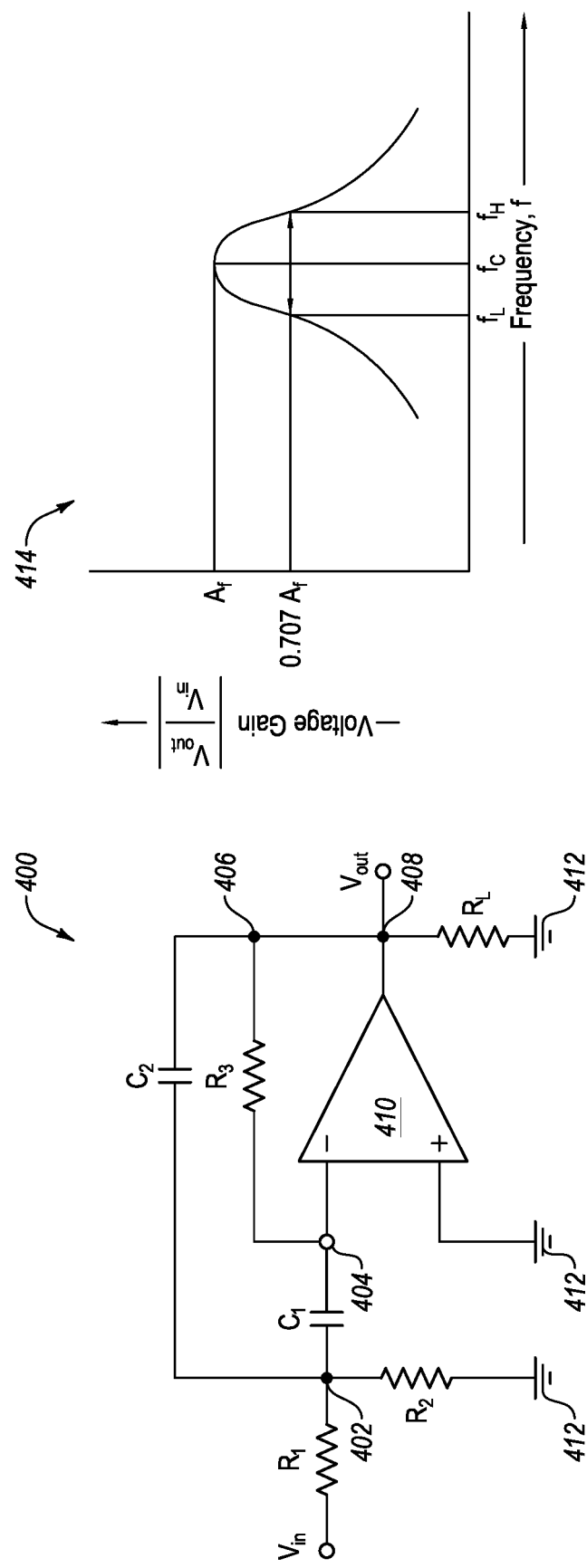
FIG. 4 illustrates an example narrow band pass filter that may be included in an acquisition circuit of FIG. 3B.

FIG. 4 illustrates an example narrow band pass filter (hereinafter "filter") 400 that may be included in the acquisition circuit 318 of FIG. 3B, arranged in accordance with at least one embodiment described herein. As illustrated in FIG. 4, the filter 400 includes an input node $V_{in}$, an output node $V_{out}$, a first intermediate node 402, a second intermediate node 404, a third intermediate node 406, a fourth intermediate node 408, an operational amplifier (opamp) 410, a first resistor $R_1$, a second resistor $R_2$, a third resistor $R_3$, a fourth resistor $R_L$, a first capacitor $C_1$, and a second capacitor $C_2$. In FIG. 4, the first resistor $R_1$ is electrically coupled between the input node $V_{in}$ and the first intermediate node 402. The second resistor $R_2$ is electrically coupled between the first intermediate node 402 and ground 412. The first capacitor $C_1$ is electrically coupled between the first intermediate node 402 and the second intermediate node 404. The second capacitor $C_2$ is electrically coupled between the first intermediate node 402 and the third intermediate node 406. The third resistor $R_3$ is electrically coupled between the second intermediate node 404 and the third intermediate node 406. An inverting input ("−" in FIG. 4) of the opamp 410 is electrically coupled to the second intermediate node 404. A non-inverting input ("+" in FIG. 4) of the opamp 410 is electrically coupled to ground 412. An output of the opamp 410 is electrically coupled to the fourth intermediate node 408. The third intermediate node 406 and the fourth intermediate node 408 are electrically coupled together. The fourth intermediate node 408 is electrically coupled to the output node $V_{out}$. The fourth resistor $R_L$ is electrically coupled between the fourth intermediate node 408 and ground 412.

FIG. 4 additionally illustrates an example frequency response 414 of the filter 400. As illustrated by the frequency response 414, the filter 400 may have a center frequency $f_C$ with a −3 decibel (dB) bandwidth between a lower frequency $f_L$ and a higher frequency $f_H$ that straddle the center frequency $f_C$. Thus, the filter 400 may generally be configured to pass signals at frequencies between the lower frequency $f_L$ and the higher frequency $f_H$ and to attenuate signals at frequencies less than the lower frequency $f_L$ and greater than the higher frequency $f_H$. In these and other embodiments, the filter 400 may be configured with the center frequency $f_C$ being about equal to a pulse repetition rate of the reflected probe radiation 314 (see FIG. 3B) to filter out optical noise at other frequencies. For instance, in some embodiments, the probe radiation 312 and thus the reflected probe radiation 314 may have a pulse repetition rate in a range of 5 MHz to 20 MHz, such as 10 MHz, and the center frequency $f_C$ of the filter 400 may be about equal thereto. Thus, optical noise in the form of, e.g., reflected therapeutic radiation which may be at a pulse repetition rate in a range from 50 Hz to 200 Hz, such as 100 Hz, may be rejected by the filter 400 of FIG. 4 and thus by the acquisition circuit 318 of FIG. 3B according to some embodiments.

Referring again to FIG. 3B, the power supply and control circuit 320 may be electrically coupled to at least one of the therapeutic radiation source 302 (or a control circuit of the therapeutic radiation source), the probe radiation source 304, and the acquisition circuit 318. The power supply and control circuit 320 may be configured to bias and modulate the probe radiation source 304, e.g., to emit pulses of probe radiation 312 with a selected pulse repetition rate, pulse duration, pulse train repetition rate, and/or pulse train duration. In these and other embodiments, the power supply and control circuit 320 may modulate the probe radiation source 304 to emit pulses of probe radiation 312 at a pulse repetition rate that is distant from a pulse repetition rate of pulses of the therapeutic radiation 310. In this and other embodiments, "distant" may indicate that the pulse repetition rate of the probe radiation 312 is at least one order of magnitude greater than the pulse repetition rate of the therapeutic radiation 310. In an example embodiment, for instance, the pulse repetition rate of the therapeutic radiation 310 may be 100 Hz and the pulse repetition rate of the probe radiation 312 may be 10 MHz, which is five orders of magnitude greater than the 100 Hz pulse repetition rate of the therapeutic radiation 310.

Referring to FIGS. 3A-3B, the systems 300A, 300B may implement any suitable detection scheme to detect the reflected probe radiation 314. For instance, one or more of the systems 300A, 300B may be arranged as an interferometric detector in which a portion of the probe radiation 312 is directed to the photodetector 306 as a local oscillator that interferes at the photodetector 306 with the reflected probe radiation 314 to generate an interference signal representative of phase of the reflected probe radiation 314. Alternatively or additionally, the portion of the probe radiation 312 directed to the photodetector 306 as the local oscillator may be frequency shifted, e.g., using an acousto-optic modulator, to facilitate a heterodyne detection scheme, rather than a homodyne detection scheme. Alternatively or additionally, photodetector 306 may be configured to generate a signal indicative of a frequency shift (or Doppler shift) of the reflected probe radiation 314 compared to the probe radiation 312. In embodiments in which frequency of the interference signal is detected, the measured quantity may not represent the phase of the reflected probe radiation 314, but rather its derivative which may correspond to a speed of a bubble wall of one or more microbubbles.

Alternatively or additionally, the probe radiation source 304 may emit a relatively short pulse with a relatively wide spectrum and/or the probe radiation source 304 may include a super luminescent diode, each of which may have a short coherence length. In this and other embodiments, a relatively short pulse may include a pulse with a period in a range from 0.01 to 1 microsecond, a relatively wide spectrum may include a spectrum of at least 40 nm—such as a spectrum defined by a central wavelength plus and minus 20 nm—and a short coherence length may include a coherence length in a range of 0.1 to 10 millimeters (mm). In embodiments in which the probe radiation source 304 has a short coherence length, a mirror or other optical element that redirects the portion of the probe radiation 312 to the photodetector 306 as the local oscillator may be displaceable, e.g., laterally in the example of FIG. 3A. The photodetector 306 may measure a signal when an optical path length of the local oscillator and of the reflected probe radiation 314 is equal. Hence, by scanning (displacing) the mirror the photodetector 306 may effectively scan the RPE layer of the eye 100 and can measure microbubbles or other phenomena across the RPE layer.

FIGS. 5A-5C illustrate first, second, and third example radiation timing sequences 500A, 500B, and 500C that may be implemented by one or both of the systems 300A, 300B of FIGS. 3A and 3B, arranged in accordance with at least one embodiment described herein. In FIGS. 5A-5C, the x-axis represents time in microseconds and the y-axis represents amplitude in arbitrary units with signal representations offset for visual clarity.

FIG. 5A includes therapeutic radiation 502, probe radiation 504, a gating signal 506, and a measurement of reflected probe radiation 508 (hereinafter "measurement 508"). The therapeutic radiation 502 may include or correspond to the therapeutic radiation 310 of FIGS. 3A-3B. The probe radiation 504 may include or correspond to the probe radiation 312 of FIGS. 3A-3B. The gating signal 506 may be applied by the acquisition circuit 318 of FIG. 3B to the photodetector 306 to gate the photodetector 306 as described elsewhere. The measurement 508 may include or correspond to a measurement of the reflected probe radiation 314 of FIGS. 3A-3B.

As illustrated in FIG. 5A, the therapeutic radiation 502 includes discrete pulses 502A. The discrete pulses 502A may have a pulse duration in a range from 1.6 microseconds to 1.8 microseconds. The therapeutic radiation 502 may be modulated to include the discrete pulses 502A at a pulse repetition rate, which may be in a range from, e.g., 50 Hz to 200 Hz, such as 100 Hz.

Analogously, the probe radiation 504 includes discrete pulses 504A, only some of which are labeled in FIG. 5A for simplicity. The discrete pulses 504A may have a pulse duration that is shorter than the pulse duration of the discrete pulses 502A of the therapeutic radiation 502 and the probe radiation 504 may be modulated to include the discrete pulses 504A at a pulse repetition rate. For instance, the pulse repetition rate of the discrete pulses 504A of the probe radiation 504 may be in a range from 5 MHz to 20 MHz, such as 10 MHz, such that the discrete pulses 504A may have a pulse duration in a range greater than zero and less than, e.g., 0.05 microseconds in the case of a 20 MHz pulse repetition rate up to less than 0.2 microseconds in the case of a 5 MHz pulse repetition rate, such as less than 0.1 microseconds in the case of a 10 MHz pulse repetition rate.

The gating signal 506 may be generated by, e.g., the acquisition circuit 318 of FIG. 3B responsive to the trigger signal from the therapeutic radiation source 302 to time synchronize the generation of the measurement 508 by the photodetector 306 and/or the acquisition circuit 318 with expected time intervals of microbubble formation and/or bursting. For instance, microbubbles may be expected to form and/or burst beginning when the eye 100 is first irradiated by any of the discrete pulses 502A of the therapeutic radiation 502 and spanning a time period that extends beyond termination of a corresponding one of the discrete pulses 502A. The time period may be in a range from four microseconds to sixteen microseconds, such as eight microseconds. Thus, the gating signal 506 may have discrete pulses 506A that start time aligned with the discrete pulses 502A and have pulse durations equal to the time period of expected microbubble formation and/or bursting.

The measurement 508 may be generated by, e.g., the photodetector 306 and/or the acquisition circuit 318 of FIG. 3B after processing the photocurrent output by the photodetector 306. In the example of FIG. 5A, because the photodetector 306 has been gated by the gating signal 506 according to expected time intervals of microbubble formation and/or bursting, the measurement 508 includes pulse trains 508A with a pulse train duration equal to a duration of the discrete pulses 506A of the gating signal. In addition, due to modulation of the probe radiation 504 to include the pulses 504A at the pulse repetition rate discussed above, the pulse trains 508A of the measurement 508 may similarly include pulses at the same pulse repetition rate as the probe radiation 504.

FIG. 5B includes the therapeutic radiation 502, probe radiation 510, reflected probe radiation 512, and a measurement of differential reflectance 514 (hereinafter "measurement 514"). The probe radiation 510 may include or correspond to the probe radiation 312 of FIGS. 3A-3B. The reflected probe radiation 512 may include or correspond to the reflected probe radiation 314 of FIGS. 3A-3B. The measurement 508 is described in more detail below.

The probe radiation 510 includes discrete pulses 510A. The discrete pulses 504A may have a pulse duration that is longer than the pulse duration of the discrete pulses 502A of the therapeutic radiation 502 and the probe radiation 510 may be modulated to include the discrete pulses 510A at a pulse repetition rate. The pulse duration of the discrete pulses 510A of the probe radiation 510 may be equal to the time period of expected microbubble formation and/or bursting, which may be in a range from four microseconds to sixteen microseconds, such as eight microseconds, in some embodiments. The pulse repetition rate of the probe radiation 510 may be equal to the pulse repetition rate of the therapeutic radiation 502 or equal to twice—or some other integer multiple of—the repetition rate of the therapeutic radiation 502. In the example of FIG. 5B, the pulse repetition rate of the probe radiation 510 is equal to twice the pulse repetition rate of the therapeutic radiation 502. For instance, if the pulse repetition rate of the therapeutic radiation 502 is 100 Hz, the pulse repetition rate of the probe radiation 510 may be 200 Hz.

As illustrated in FIG. 5B, every other discrete pulse 510A of probe radiation 510 is time aligned with a corresponding one of the discrete pulses 502A of the therapeutic radiation 502. With combined reference to FIGS. 3B and 5B, the probe radiation 510 and the therapeutic radiation 502 may be time aligned in this manner by, e.g., the power supply and control circuit 320 modulating the probe radiation source 304 to emit every other one of the discrete pulses 510A responsive to the trigger signal from the control circuit of the therapeutic radiation source 302.

The reflected probe radiation 512 includes first discrete pulses 512A reflected from the eye 100 during time intervals of microbubble formation and/or bursting that overlap with irradiation of the eye 100 by the discrete pulses 502A of the therapeutic radiation 502. The first discrete pulses 512A may have a pulse duration equal to the pulse duration of the discrete pulses 510A of the probe radiation 510 and at a pulse repetition rate equal to the pulse repetition rate of the therapeutic radiation 502.

The reflected probe radiation 512 additionally includes second discrete pulses 512B reflected from the eye 100 during time intervals without microbubble formation and/or bursting. Thus, the second discrete pulses 512B may represent a noise floor for the reflected probe radiation 512. The second discrete pulses 512B may have a pulse duration equal to the pulse duration of the discrete pulses 510A of the probe radiation 510 and at a pulse repetition rate equal to half the pulse repetition rate of the probe radiation 510 in the example of FIG. 5B.

To generate the measurement 514, each of the first pulses 512A (or photocurrent generated for each) may effectively be paired with a corresponding one of the second pulses 512B (or photocurrent generated for each) that leads or follows the first pulse 512A. Photocurrent generated for the second discrete pulse 512B in the pair may then be subtracted from the photocurrent generated for the first discrete pulse 512A in the pair. Thus, the measurement 514 may be referred to as a differential reflectance measurement.

FIG. 5C combines aspects of FIGS. 5A and 5B. In more detail, FIG. 5C includes the therapeutic radiation 502, probe radiation 516, reflected probe radiation 518, and a measurement of differential reflectance 520 (hereinafter "measurement 520"). The probe radiation 516 may include or correspond to the probe radiation 312 of FIGS. 3A-3B. The reflected probe radiation 518 may include or correspond to the reflected probe radiation 314 of FIGS. 3A-3B. The measurement 520 is described in more detail below.

The probe radiation 516 includes pulse trains 516A of discrete pulses 516B, only some of which are labeled in FIG. 5C for simplicity. The pulse trains 516A have a pulse train duration that is longer than the pulse duration of the discrete pulses 502A of the therapeutic radiation 502. The pulse train duration of the pulse trains 516A of the probe radiation 516 may be equal to the time period of expected microbubble formation and/or bursting, which may be in a range from four microseconds to sixteen microseconds, such as eight microseconds, in some embodiments. The probe radiation 516 may be modulated to include the pulse trains 516A at a pulse train repetition rate. The pulse train repetition rate of the probe radiation 516 may be equal to the pulse repetition rate of the therapeutic radiation 502 or equal to twice—or some other integer multiple of—the pulse repetition rate of the therapeutic radiation 502. In the example of FIG. 5C, the pulse train repetition rate of the probe radiation 516 is equal to twice the pulse repetition rate of the therapeutic radiation 502. For instance, if the pulse repetition rate of the therapeutic radiation 502 is 100 Hz, the pulse train repetition rate of the probe radiation 516 may be 200 Hz.

The discrete pulses 516B have a pulse duration that is shorter than the pulse duration of the discrete pulses 502A of the therapeutic radiation 502. The probe radiation 516 may be modulated to include within each of the pulse trains 516A the discrete pulses 516B at a pulse repetition rate that may be in a range from 5 MHz to 20 MHz, such as 10 MHz, in some embodiments.

As illustrated in FIG. 5C, every other pulse train 516A of probe radiation 516 is time aligned with a corresponding one of the discrete pulses 502A of the therapeutic radiation 502. With combined reference to FIGS. 3B and 5C, the probe radiation 516 and the therapeutic radiation 502 may be time aligned in this manner by, e.g., the power supply and control circuit 320 modulating the probe radiation source 304 to emit every other one of the pulse trains 516A responsive to the trigger signal from the control circuit of the therapeutic radiation source 302.

The reflected probe radiation 518 includes first pulse trains 518A reflected from the eye 100 during time intervals of microbubble formation and/or bursting that overlap with irradiation of the eye 100 by the discrete pulses 502A of the therapeutic radiation 502. The first pulse trains 518A may have a pulse train duration equal to the pulse train duration of the pulse trains 516A of the probe radiation 516 and at a pulse train repetition rate equal to the pulse repetition rate of the therapeutic radiation 502.

The reflected probe radiation 518 additionally includes second pulse trains 518B reflected from the eye 100 during time intervals without microbubble formation and/or bursting. Thus, the second pulse trains 518B may represent a noise floor for the reflected probe radiation 518. The second pulse trains 518B may have a pulse train duration equal to the pulse train duration of the pulse trains 516A of the probe radiation 516 and at a pulse train repetition rate equal to half the pulse train repetition rate of the probe radiation 516 in the example of FIG. 5C.

Insofar as the pulse trains 516A of the probe radiation 516 are made up of discrete pulses 516B, the first pulse trains 518A and the second pulse trains 518B of the reflected probe radiation 518 are similarly made up of discrete pulses with the same pulse repetition rate as the pulses 516B.

To generate the measurement 520, each of the first pulse trains 518A (or photocurrent generated for each) may effectively be paired with a corresponding one of the second pulse trains 518B (or photocurrent generated for each) that leads or follows the first pulse train 518A. Photocurrent generated for the second pulse train 518B in the pair may then be subtracted from the photocurrent generated for the first pulse train 518A in the pair. Thus, the measurement 520 may be referred to as a differential reflectance measurement.

Figure 6:
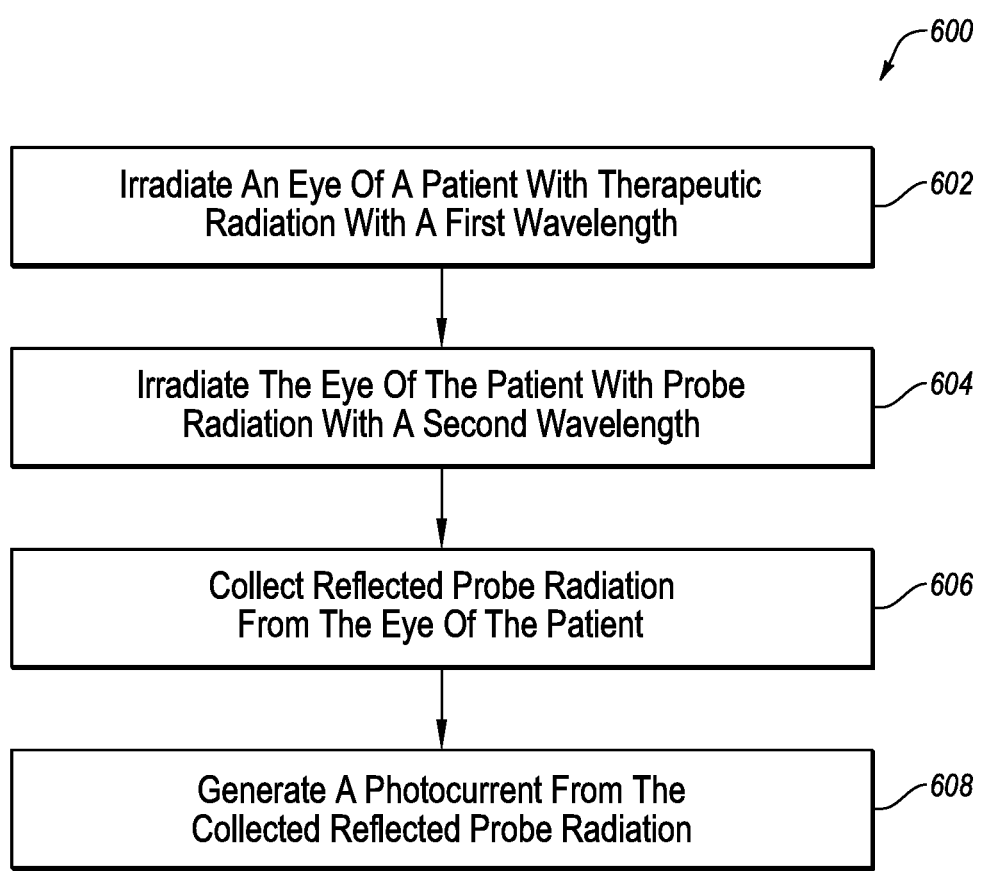
FIG. 6 illustrates a flow diagram of an example method to measure therapeutic radiation dosimetry.

FIG. 6 illustrates a flow diagram of an example method 600 to measure therapeutic radiation dosimetry, arranged in accordance with at least some embodiments described herein. The method 600 may be performed, in whole or in part, in the systems 300A, 300B and/or in other systems and configurations. Alternatively or additionally, the method 600 may be implemented by a processor device that performs or controls performance of one or more of the operations of the method 600. For instance, a computer (such as the computing device 700 of FIG. 7) or other processor device may be communicatively coupled to the system 300A or 300B and may execute software or other computer-readable instructions accessible to the computer, e.g., stored on a non-transitory computer-readable medium accessible to the computer, to perform or control the system 300A or 300B to perform the method 600 of Figure.

The method 600 may include one or more of blocks 602, 604, 606, and/or 608. Although illustrated as discrete blocks, various blocks may be divided into additional blocks, supplemented with additional blocks, combined into fewer blocks, or eliminated, depending on the particular implementation. The method 600 may begin at block 602.

In block 602 ("Irradiate An Eye Of A Patient With Therapeutic Radiation With A First Wavelength"), an eye of a patient may be irradiated with therapeutic radiation with a first wavelength. The therapeutic radiation may causes microbubbles to form on melanosomes of RPE cells of the eye of the patient. The therapeutic radiation may include, e.g., the therapeutic radiation 310 or 502 of FIG. 3A-3B or 5A-5C. Block 602 may be followed by block 604.

In block 604 ("Irradiate The Eye Of The Patient With Probe Radiation With A Second Wavelength"), the eye of the patient may be irradiated with probe radiation with a second wavelength different than the first wavelength. The probe radiation may include, e.g., the probe radiation 312, 504, 510, or 516 of FIG. 3A-3B or 5A-5C. Block 604 may be followed by block 606.

In block 606 ("Collect Reflected Probe Radiation From The Eye Of The Patient"), reflected probe radiation may be collected from the eye of the patient. The reflected probe radiation may include, e.g., the reflected probe radiation 314, 512, or 518 of FIG. 3A-3B or 5B-5C. Block 606 may be followed by block 608.

In block 608 ("Generate A Photocurrent From The Collected Reflected Probe Radiation"), a photocurrent may be generated from the collected reflected probe radiation. The photocurrent may be indicative of an amount of therapeutic radiation exposure of the eye of the patient.

For this and other procedures and methods disclosed herein, the functions or operations performed in the processes and methods may be implemented in differing order. Furthermore, the outlined operations are only provided as examples, and some of the operations may be optional, combined into fewer operations, supplemented with other operations, or expanded into additional operations without detracting from the disclosed embodiments.

For instance, the method 600 may further include gating the generating of the photocurrent according to expected time intervals of microbubble formation. In this and other embodiments, irradiating the eye of the patient with the therapeutic radiation may include controlling a therapeutic radiation source to emit discrete pulses of the therapeutic radiation. A control circuit that controls the therapeutic radiation source may provide a trigger signal to an acquisition circuit that controls the gating to gate the generating of the photocurrent when the therapeutic radiation source begins emitting a pulse of the therapeutic radiation and terminating after a first duration that is longer than a second duration of the pulse of the therapeutic radiation.

In an embodiment of the method 600, irradiating the eye of the patient with the probe radiation with the second wavelength may include irradiating the eye of the patient with a targeting optical source configured to emit the probe radiation.

In an embodiment of the method 600, irradiating the eye of the patient with the probe radiation may include emitting the probe radiation from a probe radiation source, such as the probe radiation source 304 of FIG. 3B, into a first optical path that passes through a first beam splitter, such as the first beam splitter 308A, and is redirected 90 degrees by a second beam splitter, such as the second beam splitter 308B, toward the eye of the patient. Irradiating the eye of the patient with the therapeutic radiation may include emitting the therapeutic radiation from a therapeutic radiation source, such as the therapeutic radiation source 302, into a second optical path that passes through the second beam splitter toward the eye of the patient. The method 600 may further include filtering the first optical path between the first beam splitter and the second beam splitter to block reflected therapeutic radiation with the first wavelength and to pass at least a portion of the reflected probe radiation with the second wavelength.

The method 600 may further include modulating a probe radiation source to emit the probe radiation as modulated probe radiation. Modulating the probe radiation source may include modulating the probe radiation source to emit pulses of probe radiation at a pulse repetition rate that is distant from a pulse repetition rate of pulses of the therapeutic radiation, such as at a pulse repetition rate that is at least an order of magnitude greater than the pulse repetition rate of the therapeutic radiation. Alternatively or additionally, the method 600 may further include filtering the photocurrent with a narrow band pass filter having a center frequency about equal to the pulse repetition rate of the probe radiation source.

In an embodiment of the method 600, irradiating the eye of the patient with the therapeutic radiation may include irradiating the eye of the patient with discrete pulses of the therapeutic radiation at a first pulse repetition rate. Irradiating the eye of the patient with the probe radiation may include irradiating the eye of the patient with discrete pulses of the probe radiation at a second pulse repetition rate that is faster than the first pulse repetition rate such that the reflected probe radiation comprises pulses of reflected probe radiation at the second pulse repetition rate. As described with respect to FIG. 5B, the pulses of reflected probe radiation may include first reflected pulses reflected from the eye of the patient during first periods that overlap with irradiation of the eye of the patient by the discrete pulses of the therapeutic radiation, as well as second reflected pulses reflected from the eye of the patient during second periods that do not overlap with irradiation of the eye of the patient by the discrete pulses of the therapeutic radiation. The method 600 may further include generating a differential reflectance measurement by, for each pair of a second reflected pulse of the second reflected pulses and a first reflected pulse of the first reflected pulses that leads or follows the second reflected pulse, subtracting the photocurrent generated for the second reflected pulse from the photocurrent generated for the first reflected pulse.

In an embodiment of the method 600, irradiating the eye of the patient with the therapeutic radiation may include irradiating the eye of the patient with discrete pulses of the therapeutic radiation at a pulse repetition rate. Irradiating the eye of the patient with the probe radiation may include irradiating the eye of the patient with pulse trains of discrete pulses of the probe radiation at a pulse train repetition rate that is faster than the first repetition rate such that the reflected probe radiation comprises pulse trains of reflected probe radiation at the pulse train repetition rate. As described with respect to FIG. 5C, the pulse trains of reflected probe radiation may include first reflected pulse trains reflected from the eye of the patient during first periods that overlap with irradiation of the eye of the patient by the discrete pulses of the therapeutic radiation, as well as second reflected pulse trains reflected from the eye of the patient during second periods that do not overlap with illumination of the eye of the patient by the discrete pulses of the therapeutic radiation. As further described with respect to FIG. 5B, the method 600 may further include generating a differential reflectance measurement by, for each pair of a second reflected pulse train of the second reflected pulse trains and a first reflected pulse train of the first reflected pulse trains that leads or follows the second reflected pulse train, subtracting the photocurrent generated for the second reflected pulse train from the photocurrent generated for the first reflected pulse train.

The method 600 may further include determining an exposure level of the eye of the patient to the therapeutic radiation. The method 600 may further include terminating exposure of the eye of the patient to the therapeutic radiation in response to the exposure level of the eye of the patient to the therapeutic radiation reaching and a threshold exposure level.

FIG. 7 illustrates a block diagram of an example computing device 700, in accordance with at least one embodiment of the present disclosure. The computing device 700 may be used in some embodiments to perform or control performance of one or more of the methods and/or operations described herein. For instance, the computing device may be communicatively coupled to and/or included in the system 300A or 300B of FIG. 3A or 3B to perform or control performance of the method 600 of FIG. 6. In a basic configuration 702, the computing device 700 typically includes one or more processors 704 and a system memory 706. A memory bus 708 may be used for communicating between the processor 704 and the system memory 706.

Depending on the desired configuration, the processor 704 may be of any type including, such as a microprocessor (µP), a microcontroller (µC), a digital signal processor (DSP), or any combination thereof. The processor 704 may include one or more levels of caching, such as a level one cache 710 and a level two cache 712, a processor core 714, and registers 716. The processor core 714 may include an arithmetic logic unit (ALU), a floating point unit (FPU), a digital signal processing core (DSP Core), or any combination thereof. An example memory controller 718 may also be used with the processor 704, or in some implementations, the memory controller 718 may be an internal part of the processor 704.

Depending on the desired configuration, the system memory 706 may be of any type, such as volatile memory (such as RAM), non-volatile memory (such as ROM, flash memory, or the like), or any combination thereof. The system memory 706 may include an operating system 720, one or more applications 722, and program data 724. The application 722 may include a dosimetry algorithm 726 that is arranged to measure therapeutic radiation dosimetry. The program data 724 may include control data 728 such as bias values to bias the therapeutic and/or probe radiation sources, pulse repetition rates, pulse durations, pulse train repetition rates, pulse train durations, and/or other data that may be used to control aspects of the therapeutic and/or probe radiation emitted by the system 300A or 300B of FIGS. 3A-3B. In some embodiments, the application 722 may be arranged to operate with the program data 724 on the operating system 720 to perform one or more of the methods and/or operations described herein, including those described with respect to FIG. 6.

The computing device 700 may include additional features or functionality, and additional interfaces to facilitate communications between the basic configuration 702 and any other devices and interfaces. For example, a bus/interface controller 730 may be used to facilitate communications between the basic configuration 702 and one or more data storage devices 732 via a storage interface bus 734. The data storage devices 732 may include removable storage devices 736, non-removable storage devices 738, or a combination thereof. Examples of removable storage and non-removable storage devices include magnetic disk devices such as flexible disk drives and hard-disk drives (HDDs), optical disk drives such as compact disk (CD) drives or digital versatile disk (DVD) drives, solid state drives (SSDs), and tape drives to name a few. Example computer storage media may include volatile and nonvolatile, removable and non-removable media implemented in any method or technology for storage of information, such as computer-readable instructions, data structures, program modules, or other data.

The system memory 706, the removable storage devices 736, and the non-removable storage devices 738 are examples of computer storage media. Computer storage media includes, but is not limited to, RAM, ROM, EEPROM, flash memory or other memory technology, CD-ROM, digital versatile disks (DVDs) or other optical storage, magnetic cassettes, magnetic tape, magnetic disk storage or other magnetic storage devices, or any other medium which may be used to store the desired information and which may be accessed by the computing device 700. Any such computer storage media may be part of the computing device 700.

The computing device 700 may also include an interface bus 740 for facilitating communication from various interface devices (e.g., output devices 742, peripheral interfaces 744, and communication devices 746) to the basic configuration 702 via the bus/interface controller 730. The output devices 742 include a graphics processing unit 748 and an audio processing unit 750, which may be configured to communicate to various external devices such as a display or speakers via one or more A/V ports 752. The peripheral interfaces 744 include a serial interface controller 754 or a parallel interface controller 756, which may be configured to communicate with external devices such as input devices (e.g., keyboard, mouse, pen, voice input device, touch input device, and/or others), sensors, or other peripheral devices (e.g., printer, scanner, and/or others) via one or more I/O ports 758. The communication devices 746 include a network controller 760, which may be arranged to facilitate communications with one or more other computing devices 762 over a network communication link via one or more communication ports 764.

The network communication link may be one example of a communication media. Communication media may typically be embodied by computer-readable instructions, data structures, program modules, or other data in a modulated data signal, such as a carrier wave or other transport mechanism, and may include any information delivery media. A "modulated data signal" may be a signal that includes one or more of its characteristics set or changed in such a manner as to encode information in the signal. By way of example, and not limitation, communication media may include wired media such as a wired network or direct-wired connection, and wireless media such as acoustic, radio frequency (RF), microwave, infrared (IR), and other wireless media. The term "computer-readable media" as used herein may include both storage media and communication media.

The computing device 700 may be implemented as a portion of a small-form factor portable (or mobile) electronic device such as a cell phone, a personal data assistant (PDA), a personal media player device, a wireless web-watch device, a personal headset device, an application-specific device, or a hybrid device that include any of the above functions. The computing device 700 may also be implemented as a personal computer including both laptop computer and non-laptop computer configurations.

The present disclosure is not to be limited in terms of the particular embodiments described herein, which are intended as illustrations of various aspects. Many modifications and variations can be made without departing from its spirit and scope. Functionally equivalent methods and apparatuses within the scope of the disclosure, in addition to those enumerated herein, are possible from the foregoing descriptions. Such modifications and variations are intended to fall within the scope of this disclosure. It is also to be understood that the terminology used herein is for the purpose of describing particular embodiments only, and is not intended to be limiting.

The present disclosure is not to be limited in terms of the particular embodiments described herein, which are intended as illustrations of various aspects. Many modifications and variations can be made without departing from its spirit and scope. Functionally equivalent methods and apparatuses within the scope of the disclosure, in addition to those enumerated herein, are possible from the foregoing descriptions. Such modifications and variations are intended to fall within the scope of this disclosure. Also, the terminology used herein is for the purpose of describing particular embodiments only, and is not intended to be limiting.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

In general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation, no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general, such a construction is intended in the sense one having skill in the art would understand the convention (e.g., "a system having at least one of A, B, and C" would include but not be limited to systems that include A alone, B alone, C alone, A and B together, A and C together, B and C together, and/or A, B, and C together, etc.). In those instances where a convention analogous to "at least one of A, B, or C, etc." is used, in general, such a construction is intended in the sense one having skill in the art would understand the convention (e.g., "a system having at least one of A, B, or C" would include but not be limited to systems that include A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

For any and all purposes, such as in terms of providing a written description, all ranges disclosed herein also encompass any and all possible sub ranges and combinations of sub ranges thereof. Any listed range can be easily recognized as sufficiently describing and enabling the same range being broken down into at least equal halves, thirds, quarters, fifths, tenths, and/or others. As a non-limiting example, each range discussed herein can be readily broken down into a lower third, middle third and upper third, etc. All language such as "up to," "at least," and the like include the number recited and refer to ranges which can be subsequently broken down into sub ranges as discussed above. Finally, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

From the foregoing, various embodiments of the present disclosure have been described herein for purposes of illustration, and various modifications may be made without departing from the scope and spirit of the present disclosure. Accordingly, the various embodiments disclosed herein are not intended to be limiting.

What is claimed is:

1. A laser-based ophthalmological surgical system, comprising:
    a therapeutic radiation source configured to emit therapeutic radiation with a first wavelength;
    a probe radiation source configured to emit probe radiation with a second wavelength different than the first wavelength;
    one or more optical elements configured to direct the therapeutic radiation and the probe radiation into an eye of a patient and to collect reflected probe radiation from the eye of the patient, the reflected probe radiation being indicative of an amount of therapeutic radiation exposure on the eye of the patient;
    a photodetector configured to receive the reflected probe radiation from the one or more optical elements and to generate a photocurrent indicative of the amount of therapeutic radiation exposure on the eye of the patient;
    an acquisition circuit electrically coupled to the photodetector and configured to gate the photodetector according to expected time intervals of microbubble formation and/or microbubble burst in the eye of the patient; and
    an optical filter positioned in a first optical path and configured to block the reflected therapeutic radiation with the first wavelength and to pass the reflected probe radiation with the second wavelength.

2. The laser-based ophthalmological surgical system of claim 1, further comprising a control circuit configured to operate the therapeutic radiation source to emit a pulse of therapeutic radiation that has a first duration,
    wherein the acquisition circuit is electrically coupled to the control circuit and is configured to receive a trigger signal from the control circuit to gate the photodetector to generate photocurrent for a second duration that initiates when the therapeutic radiation source emits the pulse of therapeutic radiation, wherein the second duration is longer than the first duration.

3. The laser-based ophthalmological surgical system of claim 2, wherein:
    the acquisition circuit is configured to gate the photodetector for the second duration to have a range from 4 microseconds to 16 microseconds; and
    the control circuit is configured to control the first duration to have a range from 1.6 microseconds to 1.8 microseconds.

4. The laser-based ophthalmological surgical system of claim 1, wherein the one or more optical elements comprise a second beam splitter in a second optical path of the therapeutic radiation between the therapeutic radiation source and the eye of the patient and in the first optical path between a first beam splitter and the eye of the patient, wherein the second beam splitter is configured to:
    pass at least a portion of the therapeutic radiation from the therapeutic radiation source;
    reflect at least a portion of the probe radiation toward the eye of the patient; and
    reflect at least a portion of the reflected probe radiation collected from the eye of the patient toward the first beam splitter.

5. The laser-based ophthalmological surgical system of claim 1, further comprising a control circuit electrically coupled to the probe radiation source and configured to modulate the probe radiation source.

6. The laser-based ophthalmological surgical system of claim 5, wherein the acquisition circuit is electrically coupled to the control circuit, and
    wherein the acquisition circuit is configured to gate the photodetector according to expected time intervals of microbubble formation on melanosomes of retinal pigment epithelial (RPE) cells of the eye of the patient in response to exposure to the therapeutic radiation.

7. The laser-based ophthalmological surgical system of claim 6, wherein the acquisition circuit comprises a narrow band pass filter having a center frequency about equal to a pulse repetition rate of pulses of the probe radiation source.

8. The laser-based ophthalmological surgical system of claim 1, further comprising a power supply and control circuit electrically coupled to the probe radiation source and configured to bias and modulate the probe radiation source to emit pulses of probe radiation at a pulse repetition rate that is different from a pulse repetition rate of pulses of therapeutic radiation.

9. The laser-based ophthalmological surgical system of claim 1, further comprising a control circuit coupled to the probe radiation source,
    wherein the control circuit is configured to modulate the probe radiation source to emit pulses of probe radiation at a pulse repetition rate of at least 100 kilohertz (kHz).

10. A method to measure therapeutic radiation dosimetry, the method comprising:
    irradiating an eye of a patient with therapeutic radiation with a first wavelength, wherein the therapeutic radiation causes microbubbles to form on melanosomes of retinal pigment epithelial (RPE) cells of the eye of the patient;
    irradiating the eye of the patient with probe radiation with a second wavelength different than the first wavelength;
    collecting reflected probe radiation from the eye of the patient;
    filtering a first optical path to block reflected therapeutic radiation with the first wavelength and to pass at least a portion of the reflected probe radiation with the second wavelength;
    generating a photocurrent from the collected reflected probe radiation, the photocurrent being indicative of an amount of therapeutic radiation exposure of the eye of the patient; and
    gating the generating of the photocurrent according to expected time intervals of microbubble formation.

11. The method of claim 10, further comprising:
    irradiating the eye of the patient with the therapeutic radiation by a control circuit that controls a therapeutic radiation source to emit a pulse of therapeutic radiation that has a first duration; and controlling the therapeutic radiation source by providing a trigger signal from the control circuit to an acquisition circuit that controls gating the generating of the photocurrent for a second duration that initiates when the therapeutic radiation source emits the pulse of therapeutic radiation, wherein the second duration is longer than the first duration.

12. The method of claim 11, further comprising:
controlling the first duration to have a range from 1.6 microseconds to 1.8 microseconds; and
controlling the second duration to have a range of 4 microseconds to 16 microseconds.

13. The method of claim 10, wherein irradiating the eye of the patient with the probe radiation with the second wavelength comprises irradiating the eye of the patient with a targeting optical source configured to emit the probe radiation with a center wavelength in a range of 590 to 750 nanometers (nm), and
wherein irradiating the eye of the patient with the therapeutic radiation with the first wavelength comprises irradiating the eye of the patient with the therapeutic radiation with a center wavelength in a range from 520 to 540 nm.

14. The method of claim 10, further comprising modulating a probe radiation source to emit the probe radiation as modulated probe radiation.

15. The method of claim 14, wherein modulating the probe radiation source comprises modulating the probe radiation source to emit pulses of probe radiation at a pulse repetition rate that is different from a pulse repetition rate of pulses of therapeutic radiation.

16. The method of claim 15, wherein modulating the probe radiation source to emit the pulses of probe radiation at the pulse repetition rate that is different from the pulse repetition rate of the pulses of therapeutic radiation comprises modulating the probe radiation source to emit the pulses of probe radiation at a pulse repetition rate that is at least an order of magnitude greater than the pulse repetition rate of the therapeutic radiation.

17. The method of claim 10, wherein:
irradiating the eye of the patient with the therapeutic radiation comprises irradiating the eye of the patient with discrete pulses of therapeutic radiation at a first pulse repetition rate;
irradiating the eye of the patient with the probe radiation comprises irradiating the eye of the patient with discrete pulses of probe radiation at a second pulse repetition rate that is faster than the first pulse repetition rate such that the reflected probe radiation comprises pulses of reflected probe radiation at the second pulse repetition rate including:

first reflected pulses reflected from the eye of the patient during first periods that overlap with irradiation of the eye of the patient by the discrete pulses of therapeutic radiation; and
second reflected pulses reflected from the eye of the patient during second periods that do not overlap with irradiation of the eye of the patient by the discrete pulses of therapeutic radiation; and
the method further comprises generating a differential reflectance measurement by, for each pair of a second reflected pulse of the second reflected pulses and a first reflected pulse of the first reflected pulses that leads or follows the second reflected pulse, subtracting the photocurrent generated for the second reflected pulse from the photocurrent generated for the first reflected pulse.

18. The method of claim 10, wherein:
irradiating the eye of the patient with the therapeutic radiation comprises irradiating the eye of the patient with discrete pulses of therapeutic radiation at a first pulse repetition rate;
irradiating the eye of the patient with the probe radiation comprises irradiating the eye of the patient with pulse trains of discrete pulses of probe radiation at a pulse train repetition rate that is faster than the first pulse repetition rate such that the reflected probe radiation comprises pulse trains of reflected probe radiation at the pulse train repetition rate including:

first reflected pulse trains reflected from the eye of the patient during first periods that overlap with irradiation of the eye of the patient by the discrete pulses of therapeutic radiation; and
second reflected pulse trains reflected from the eye of the patient during second periods that do not overlap with irradiation of the eye of the patient by the discrete pulses of therapeutic radiation; and
the method further comprises generating a differential reflectance measurement by, for each pair of a second reflected pulse train of the second reflected pulse trains and a first reflected pulse train of the first reflected pulse trains that leads or follows the second reflected pulse train, subtracting the photocurrent generated for the second reflected pulse train from the photocurrent generated for the first reflected pulse train.

19. The method of claim 10, wherein the filtering is performed by an optical filter positioned in the first optical path.

* * * * *